(12) United States Patent
Barak et al.

(10) Patent No.: US 7,572,888 B2
(45) Date of Patent: Aug. 11, 2009

(54) METHODS OF ASSAYING RECEPTOR ACTIVITY AND CONSTRUCTS USEFUL IN SUCH METHODS

(75) Inventors: Lawrence S. Barak, Durham, NC (US); Marc G. Caron, Hillsborough, NC (US); Stephen S. Ferguson, London (CA); Jie Zhang, Wallingford, CT (US)

(73) Assignee: Duke University, Durham, NC (US)

( * ) Notice: Subject to any disclaimer, the term of this patent is extended or adjusted under 35 U.S.C. 154(b) by 197 days.

(21) Appl. No.: 10/785,841

(22) Filed: Feb. 24, 2004

(65) Prior Publication Data

US 2004/0209308 A1     Oct. 21, 2004

Related U.S. Application Data

(63) Continuation of application No. 09/772,644, filed on Jan. 30, 2001, now Pat. No. 6,770,449, which is a continuation of application No. 09/469,554, filed on Dec. 22, 1999, now Pat. No. 6,528,271, which is a continuation-in-part of application No. 09/233,530, filed on Jan. 20, 1999, now Pat. No. 6,110,693, which is a continuation of application No. 08/869,568, filed on Jun. 5, 1997, now Pat. No. 5,891,646.

(51) Int. Cl.
C07K 14/00 (2006.01)
C07K 17/00 (2006.01)
G01N 33/53 (2006.01)
G01N 33/567 (2006.01)

(52) U.S. Cl. .................. 530/350; 435/7.1; 435/7.2
(58) Field of Classification Search ................. 435/7.1, 435/7.2; 530/350
See application file for complete search history.

(56) References Cited

U.S. PATENT DOCUMENTS

| | | | |
|---|---|---|---|
| 3,654,090 A | 4/1972 | Schuurs et al. |
| 3,850,752 A | 11/1974 | Schuurs et al. |
| 4,016,043 A | 4/1977 | Schuurs et al. |
| 4,219,335 A | 8/1980 | Ebersole |
| 4,324,633 A | 4/1982 | Lovejoy |
| 4,341,761 A | 7/1982 | Ganfield et al. |
| RE31,006 E | 8/1982 | Schuurs et al. |
| 4,342,566 A | 8/1982 | Theofilopoulos et al. |
| 4,399,121 A | 8/1983 | Albarella et al. |
| 4,426,330 A | 1/1984 | Sears |
| 4,427,783 A | 1/1984 | Newman et al. |
| 4,444,887 A | 4/1984 | Hoffmann |
| 4,451,570 A | 5/1984 | Royston et al. |
| 4,466,917 A | 8/1984 | Nussenzweig et al. |
| 4,472,500 A | 9/1984 | Milstein et al. |
| 4,491,632 A | 1/1985 | Wands et al. |
| 4,493,795 A | 1/1985 | Nestor, Jr. et al. |
| 4,493,890 A | 1/1985 | Morris |
| 4,534,899 A | 8/1985 | Sears |
| 4,816,397 A | 3/1989 | Boss et al. |
| 4,816,567 A | 3/1989 | Cabilly et al. |
| 4,908,773 A | 3/1990 | Pantoliano et al. |
| 4,981,784 A | 1/1991 | Evans et al. |
| 5,034,506 A | 7/1991 | Summerton et al. |
| 5,264,221 A | 11/1993 | Tagawa et al. |
| 5,284,746 A | 2/1994 | Sledziewski et al. |
| 5,324,633 A | 6/1994 | Fodor et al. |
| 5,352,660 A | 10/1994 | Pawson |
| 5,366,889 A | 11/1994 | MacDonald et al. |
| 5,462,856 A | 10/1995 | Lerner et al. |
| 5,468,854 A | 11/1995 | McCabe et al. |
| 5,482,835 A | 1/1996 | King et al. |
| 5,491,084 A | 2/1996 | Chalfie et al. |
| 5,522,896 A | 6/1996 | Prescott |
| 5,532,157 A | 7/1996 | Fink |
| 5,539,082 A | 7/1996 | Nielsen et al. |
| 5,541,309 A | 7/1996 | Prasher |
| 5,569,824 A | 10/1996 | Donehower et al. |
| 5,569,827 A | 10/1996 | Kessous-Elbaz et al. |
| 5,574,656 A | 11/1996 | Agrafiotis et al. |
| 5,575,997 A | 11/1996 | Leung et al. |
| 5,576,436 A | 11/1996 | McCabe et al. |
| 5,578,079 A | 11/1996 | Kamel et al. |
| 5,582,834 A | 12/1996 | Leung et al. |

(Continued)

FOREIGN PATENT DOCUMENTS

WO     WO88/03168 A1     5/1988

(Continued)

OTHER PUBLICATIONS

Attramadal et al. (1992) Beta-arestin2, a novel member of the arrestin/beta-arrestin gene family. J. Biol. Chem. 267(25): 17882-17890.*

(Continued)

Primary Examiner—Anne-Marie Falk
(74) Attorney, Agent, or Firm—Gargi Talukder; David J. Brezner; Morgan Lewis & Bockius LLP

(57) ABSTRACT

Described are methods of detecting G-protein coupled receptor (GPCR) activity in vivo and in vitro; methods of assaying GPCR activity; and methods of screening for GPCR ligands, G protein-coupled receptor kinase (GRK) activity, and compounds that interact with components of the GPCR regulatory process. Constructs useful in such methods are described.

9 Claims, 14 Drawing Sheets

U.S. PATENT DOCUMENTS

| | | |
|---|---|---|
| 5,591,618 A | 1/1997 | Chantry et al. |
| 5,597,699 A | 1/1997 | Lanzara |
| 5,602,240 A | 2/1997 | De Mesmaeker et al. |
| 5,625,048 A | 4/1997 | Tsien et al. |
| 5,627,039 A | 5/1997 | Pereira-Smith et al. |
| 5,658,783 A | 8/1997 | Grandy et al. |
| 5,661,184 A | 8/1997 | Helton et al. |
| 5,665,710 A | 9/1997 | Rahman et al. |
| 5,670,113 A | 9/1997 | Akong et al. |
| 5,684,711 A | 11/1997 | Agrafiotis et al. |
| 5,700,673 A | 12/1997 | McElroy et al. |
| 5,705,335 A | 1/1998 | Hendry |
| 5,714,331 A | 2/1998 | Buchardt et al. |
| 5,719,262 A | 2/1998 | Buchardt et al. |
| 5,744,313 A | 4/1998 | Williams et al. |
| 5,767,337 A | 6/1998 | Roses et al. |
| 5,770,176 A | 6/1998 | Nargessi |
| 5,777,079 A | 7/1998 | Tsien et al. |
| 5,804,387 A | 9/1998 | Cormack et al. |
| 5,821,067 A | 10/1998 | Grandy et al. |
| 5,854,004 A | 12/1998 | Czernilofsky et al. |
| 5,856,111 A | 1/1999 | Ullrich et al. |
| 5,864,488 A | 1/1999 | Isaacs et al. |
| 5,874,219 A | 2/1999 | Rava et al. |
| 5,882,944 A | 3/1999 | Sadée |
| 5,912,122 A | 6/1999 | Daggett et al. |
| 5,912,137 A | 6/1999 | Tsien et al. |
| 5,912,138 A | 6/1999 | Tonks et al. |
| 5,919,646 A | 7/1999 | Okun et al. |
| 5,958,713 A | 9/1999 | Thastrup et al. |
| 5,968,750 A | 10/1999 | Zolotukhin et al. |
| 5,972,629 A | 10/1999 | Niman |
| 5,972,639 A | 10/1999 | Parandoosh |
| 5,987,390 A | 11/1999 | Ladunga |
| 5,989,835 A | 11/1999 | Dunlay et al. |
| 5,998,204 A | 12/1999 | Tsien et al. |
| 6,007,986 A | 12/1999 | Sadée |
| 6,017,496 A | 1/2000 | Nova et al. |
| RE36,547 E | 2/2000 | Crain et al. |
| 6,025,129 A | 2/2000 | Nova et al. |
| 6,027,890 A | 2/2000 | Ness et al. |
| 6,028,175 A | 2/2000 | Grandy et al. |
| 6,051,386 A | 4/2000 | Lerner et al. |
| 6,057,114 A | 5/2000 | Akong et al. |
| 6,066,476 A | 5/2000 | Tsien et al. |
| 6,087,115 A | 7/2000 | Gershengorn et al. |
| 6,096,756 A | 8/2000 | Crain et al. |
| 6,100,026 A | 8/2000 | Nova et al. |
| 6,100,042 A | 8/2000 | Fowlkes et al. |
| 6,103,492 A | 8/2000 | Yu |
| 6,107,324 A | 8/2000 | Behan et al. |
| 6,124,102 A | 9/2000 | Fodor et al. |
| 6,127,133 A | 10/2000 | Akong et al. |
| 6,140,509 A | 10/2000 | Behan et al. |
| 6,150,393 A | 11/2000 | Behan et al. |
| 6,255,059 B1 | 7/2001 | Klein et al. |
| 2003/0009022 A1* | 1/2003 | Klein et al. ............ 536/23.5 |

FOREIGN PATENT DOCUMENTS

| | | |
|---|---|---|
| WO | WO93/24510 A1 | 12/1993 |
| WO | WO94/16684 | 8/1994 |
| WO | WO94/16684 A1 | 8/1994 |
| WO | WO94/26764 A1 | 11/1994 |
| WO | WO95/21191 | 8/1995 |
| WO | WO96/23810 | 8/1996 |
| WO | WO96/23898 | 8/1996 |
| WO | WO96/27027 | 9/1996 |
| WO | WO96/27675 | 9/1996 |
| WO | WO96/40062 A1 | 12/1996 |
| WO | WO97/11091 | 3/1997 |
| WO | WO98/12310 | 3/1998 |
| WO | WO98/44350 A1 | 10/1998 |
| WO | WO98/55635 A2 | 12/1998 |
| WO | WO99/66324 A2 | 12/1999 |
| WO | WO00/12704 A2 | 3/2000 |

OTHER PUBLICATIONS

U.S. Appl. No. 09/201,396, filed Jan. 9, 2003, Klein, et al.

U.S. Appl. No. 08/689,172, filed Aug. 6, 1996, Klein, C, et al., abandoned, listed in child U.S. Appl. No. 09/201,396.

U.S. Appl. No. 08/587,895, filed Jan. 17, 1996, Klein, C, et al., abandoned, listed in child U.S. Appl. No. 09/201,396.

U.S. Appl. No. 08/309,313, filed Sep. 20, 1994, Fowlkes, et al., abandoned, listed in child U.S. Appl. No. 09/201,396 and patents 6,255,059 and 6,100,042.

U.S. Appl. No. 08/190,328, filed Jan. 31, 1994, Fowlkes, et al., abandoned, listed in child U.S. Appl. No. 09/201,396 and patents 6,255,059 and 6,100,042.

U.S. Appl. No. 08/041,431, filed Mar. 31, 1993, Fowlkes, et al., abandoned, listed in child U.S. Appl. No. 09/201,396 and patents 6,255,059 and 6,100,042.

Atlas, D., et al., *Probing of β-adrenergic receptors by novel fluorescent β-adrenergic blockers*, Proceedings of the National Academy of Sciences, vol. 74, No. 12, Dec. 1977, pp. 5290-5294, Proc. Natl Acad. Sci, USA.

Angers, S., et al., *Detection of $β_2$-Adrenergic receptor dimerization in living cells using bioluminescence resonance energy transfer (BRET)*, Proceedings of the National Academy of Sciences, vol. 97, No. 7, Mar. 28, 2000, pp. 3684-3689, Proc. Natl Acad. Sci, USA.

Barak, L.S., et al., *Constitutive arrestin-mediated desensitization of a human vasopressin receptor mutant associated with nephrogenic diabetes insipidus*, published Dec. 26, 2000, Proc. Natl. Acad. Sci USA Online, and Proceedings of the National Academy of Sciences, vol. 98, No. 1, Jan. 2, 2001, pp. 93-98.

Barak, L.S., et al., *Real-time Visualization of the Cellular Redistribution of G Protein-coupled Receptor Kinase 2 and β-arrestin 2 during Homologous Desensitization of the Substance P Receptor*, Journal of Biological Chemistry, vol. 274, No. 11, Mar. 12, 1999, pp. 7565-7569, The American Society of Biochemistry and Molecular Biology, Inc., USA.

Barak, L.S., et al., *Characterization of a Green Fluorescent Protein Conjugated $Beta_2$-Adrenergic Receptor*, Molecular Biology of the Cell (supplement), Abstract #2484, vol. 7, p. 427a (Dec. 1996).

Bardram, L., et al., *Processing-Independent Radioimmunoanalysis: A General Analytical Principle Applied to Progastrin and Its Products*, Anal Biochem, vol. 175, pp. 537-543, 1988, Academic Press, Inc.

Benovic, J.L., et al., *Regulation of Adenylyl Cyclase-Coupled β-Adrenergic Receptors*, Annual Review Cell Biology, vol. 4, pp. 405-428, 1988, Annual Reviews, Inc.

Bohn, Laura M., et al., *Enhanced Morphine Analgesia in Mice Lacking β-Arrestin 2*, Science, (Washington D.C.), vol. 286, No. 5449, Dec. 24, 1999, pp. 2495-2498.

Brady, III, C.E., *Secretin Provocation Test in the Diagnosis of Zollinger-Ellison Syndrome*, The American Journal of Gastroenterology, vol. 86, pp. 129-134, Feb. 1991, USA.

Bugat, R., et al., *Gastric Mucosal Lesions Produced By Intravenous Infusion of Aspirin in Cats*, Gastroenterology, vol. 71, pp. 754-759, Nov. 1976, USA.

Carey, K.L., et al., *Evidence Using a Green Fluorescent Protein-Glucocorticoid Receptor Chimera that the RAN/TC4 GTPase Mediates an Essential Function Independent of Nuclear Protein Import*, The Journal of Cell Biology, vol. 133, pp. 985-996, 1996, The Rockefeller University Press, USA.

Chalfie, M., et al., *Green fluorescent protein as a Marker for Gene Expression*, Science, vol. 263, pp. 802-805 (1994).

Chen, Jeannie, et al., *Increased Susceptibility to Light Damage in an Arrestin Knockout Mouse Model of Oguchi Disease (Stationary Night Blindness)*, Investigative Ophthalmology & Visual Science, vol. 40, No. 12, Nov. 1999, pp. 2978-2982.

Cox, B.M., *Mechanisms of Tolerance, Opioids in Pain Control: Basic and Clinical Aspects*, Ch. 6, pp. 109-130 (1999). Cambridge University Press.

*Current Protocols in Molecular Biology*, vol. 1, Section II, Supplement 24, 6.3.1-6.3.6, 1993, John Wiley & Sons, N.Y.

Czerwinski, G., et al., *Cytotoxic agents directed to peptide hormone receptors: Defining the requirements for a successful drug*, Proceedings of the National Academy of Sciences, vol. 95, Sep. 1998, pp. 11520-11525, Proc. Natl. Acad. Sci, USA.

Daulhac, L., et al., *Src-family Tyrosine Kinases in Activation of ERK-1 and p85/p110-phosphatidylinositol 3-Kinase by G/CCK$_B$ Receptors*, Journal of Biological Chemistry, vol. 274, No. 29, Jul. 16, 1999, pp. 20657-20663, The American Society of Biochemistry and Molecular Biology, Inc., USA.

Drews, J., *Drug Discovery: A Historical Perspective*, Science, vol. 287, Mar. 17, 2000, pp. 1960-1964, American Association for the Advancement of Science, Washington, D.C.

Edkins, J.S., *On the Chemical Mechanism of Gastric Secretion*, Proc R Soc Lond [Biol], vol. 76, p. 376, 1905.

Ferguson, S.S.G., et al., *G-protein-coupled receptor regulation: role of G-protein-coupled kinases and arrestins*, Can. J. Physiol. Pharmacol., vol. 74, 1996, pp. 1095-1110, NRC, Canada.

Ganguli, P.C., et al., *Radioimmunoassay of Plasma-Gastrin In Pernicious Anaemia, Achlorhydria Without Pernicious Anaemia, Hypochlorhydria, and in Controls*, The Lancet, vol. 1, pp. 155-158, Jan. 23, 1971.

Grady, E., et al., *Mechanisms Attenuating Cellular Responses to Neuropeptides: Extracellular Degradation of Ligands and Desensitization of Receptors*, The Journal of Investigative Dermatology Symposium Proceedings, vol. 21, No. 1, pp. 69-75, Aug. 1997, The Society of Investigative Dermatology, Inc.

Gregory, R.A., et al., *The constitution and properties of two gastrins extracted from hog antral mucosa*, Gut, vol. 5, pp. 103-117, 1964.

Grisshammer, R., et al., *Expression of rat NK-2 (neurokinin A) receptor in E. coli*, Receptor Channels, vol. 2, pp. 295-302 (1994) Abstract.

Grisshammer, R., et al., *Expression of a rat neurotensin receptor in Escherichia coli*, Biochem. J., vol. 295, pp. 571-576, Oct. 1993, Abstract.

Gurevich, V.V., et al., *Arrestin Interactions with G Protein-coupled Receptors*, Journal of Biological Chemistry, vol. 270, No. 2, pp. 720-731, 1995, The American Society for Biochemistry and Molecular Biology, Inc., USA.

Gurevich, V.V., et al., *Binding of Wild Type and Chimeric Arrestins to the m2 Muscarinic Cholinergic Receptor*, Journal of Biological Chemistry, vol. 268, No. 23, pp. 16879-16882, 1993, The American Society for Biochemistry and Molecular Biology, Inc., USA.

Gurevich, V.V., et al., *Visual Arrestin Interaction with Rhodopsin*, Journal of Biological Chemistry, vol. 268, No. 16, pp. 11628-11638, 1993, The American Society for Biochemistry and Molecular Biology, Inc., USA.

Hanninen, A.L., et al., *Expression in Escherichia coli of rat neurotensin receptor fused to membrane proteins from the membrane-containing bacteriophage PRD1*, Biol. Chem. Hoppe Seyler, vol. 375, pp. 833-836 (1994) Abstract.

Harada, A., et al., *Altered microtubule organization in small-calibre axons of mice lacking tau protein*, Nature, vol. 369, No. 6480, pp. 488-491, Jun. 9, 1994, Macmillian Magazines, Ltd., London.

Harden, T.K., *Agonist-induced Desensitization of the β-Adrenergic Receptor-linked Adenylate Cyclase*, Pharmacological Reviews, vol. 35, No. 1, pp. 5-32, 1983, USA.

Hausdorff, W.P., et al., *A Mutation of the $\beta_2$-Adrenergic Receptor Impairs Agonist Activation of Adenylyl Cylclase Without Affecting High Affinity Agonist Binding*, Journal of Biological Chemistry, vol. 265, No. 3, Jan. 25, 1990, pp. 1388-1393, The American Society for Biochemistry and Molecular Biology, Inc. USA.

Hersey, S.J., et al., *Gastric Acid Secretion*, Physiological Reviews, vol. 75, No. 1, 1995, pp. 155-189, USA.

Htun, H., et al., *Visualization of glucocorticoid Receptor Translocation and Intranuclear Organization in Living Cells with a Green Fluorescent Protein Chimera*, Proceedings of the National Academy of Sciences, May 1996, vol. 93, pp. 4845-4850, USA.

Hughes, J., et al., *Development of a class of selective cholecystokinin type B receptor antagonists having potent anxiolytic activity*, Proceedings of the National Academy of Sciences, vol. 87, Sep. 1990, pp. 6728-6732, Proc. Natl. Acad. Sci, USA.

Joshi, S.N., et al., *Gastrin and Colon Cancer: A Unifying Hypothesis*, Digestive Diseases, vol. 14, pp. 334-344, 1996.

Kaether, C., et al., *Visualization of protein transport along the secretory pathway using green fluorescent protein*, FEBS Letters, vol. 369, pp. 267-271, 1995.

Keith, D.E., et al., *Morphine Activates Opioid Receptors without Causing their Rapid Internalization*, Journal of Biological Chemistry, vol. 271, No. 32, pp. 19021-19024, 1996, American Society for Biochemistry and Molecular Biology, Inc., USA.

Klein, U., et al., *A Novel Interaction between Adrenergic Receptors and the α-Subunit of Eukaryotic Initiation Factor 2B*, Journal of Biological Chemistry, vol. 272, No. 31, Aug. 1, 1997, pp. 19099-19102, American Society for Biochemistry and Molecular Biology, Inc., USA.

Kopin, A.S., et al., *Expression cloning and characterization of the canine parietal cell gastrin receptor*, Proceedings of the National Academy of Sciences, vol. 89, Apr. 1992, pp. 3605-3609, Proc. Natl. Acad. Sci, USA.

Kovoor, Abraham, et al., *μ and δ Opioid Receptors Are Differentially Desensitized by the Coexpression of β-Adrenergic Receptor Kinase 2 and β-Arrestin 2 in Xenopus Oocytes*, The Journal of Biological Chemistry, (U.S.A.), vol. 272, No. 44, Oct. 31, 1997, pp. 27605-27611.

Laporte, S. A., et al., *The Interaction of β-Arrestin with the AP-2 Adaptor Is Required for Clustering of $\beta_2$-Adrenergic Receptor into Clathrin-coated Pits*, published Apr. 17, 2000, JBC Papers in Press, and Journal of Biological Chemistry, vol. 275, No. 30, Jul. 28, 2000, pp. 23120-23126, The American Society for Biochemistry and Molecular Biology, Inc., USA.

Laporte, S.A., et al., *The $\beta_2$-Adrenergic Receptor/βarrestin complex recruits the clathrin adaptor AP-2 during endocytosis*, Proceedings of the National Academy of Sciences, vol. 96, No. 7, Mar. 30, 1999, pp. 3712-3717, Proc. Natl. Acad. Sci, USA.

Lee, Y.M., et al., *The Human Brain Cholecystokinin-B/Gastrin Receptor*, Journal of Biological Chemistry, vol. 268, No. 11, Apr. 15, 1993, pp. 8164-8169, The American Society of Biochemistry and Molecular Biology, Inc., USA.

Lefkowitz, et al., *Adenylate Cyclase-coupled Beta-Adrenergic Receptors: Structure and Mechanisms of Activation and Desensitization*, Ann. Rev. Biochem, vol. 52, pp. 159-186, 1983, Annual Reviews Inc.

Lefkowitz, R.J., *G Protein-coupled Receptors, III. New Roles For Receptor Kinases and β-arrestins in Receptor Signaling and Desensitization*, Journal of Biological Chemistry, vol. 273, No. 30, Jul. 24, 1998, pp. 18677-18680, The American Society of Biochemistry and Molecular Biology, Inc., USA.

Leopoldt, D., et al., *Gβγ Stimulates Phosphoinositide 3-Kinase-γ by Direct Interaction with Two Domains of the Catalytic p110 Subunit*, Journal of Biological Chemistry, vol. 273, No. 12, Mar. 20, 1998, pp. 7024-7029.

Luttrell, L.M., et al., *βarrestin-Dependent Formation of $\beta_2$ Adrenergic Receptor-Src Protein Kinase Complexes*, vol. 283, Jan. 29, 1999, Science, pp. 655-661, USA.

Mantyh, C.R., et al., *Localization of Cholecystokinin A and Cholecystokinin B/Gastrin Receptors in the Canine Upper Gastrointestinal Tract*, Gastroenterology, vol. 107, 1994, pp. 1019-1030, American Gastroenterological Association, USA.

Mathier, Michael, A. et al., *Enhanced Left Ventricular Contractile Responses to Acute β-Adrenergic Stimulation in a β-Arrestin 1 Knockout Mouse*, Circulation, 70$^{th}$ Scientific Sessions of the American Heart Association, Orlando, Florida, US, vol. 96, No. 8, Suppl., 1997, p. 1445.

McConalogue, K., et al., *Activation and Internalization of the μ-opioid Receptor by the Newly Discovered Endogenous Agonists, Endomorphin-1 and Endomorphin-2*, Neuroscience, vol. 90, No. 3, pp. 1051-1059, 1999, Elsevier Science Ltd., Great Britain.

McConalogue, K., et al., *G Protein-Coupled Receptors in Gastrointestinal Physiology II. Regulation of neuropeptide receptors in enteric neurons*, American J. Physiol., vol. 274, pp. G792-G796, 1998, American Physiological Society.

McConalogue, K., et al., *Substance P-induced Trafficking of β-arrestins*, Journal of Biological Chemistry, vol. 274, No. 23, pp. 16257-16268, Jun. 4, 1999, The American Society for Biochemistry and Molecular Biology, Inc., USA.

Ménard, L., et al., *Synergistic Regulation of $β_2$-Adrenergic Receptor Sequestration: Intracellular Complement of $β_2$-Adrenergic Receptor Kinase and β-Arrestin Determine Kinetics of Internalization*, Molecular Pharmacology, vol. 51, No. 5, May 1997, pp. 800-808, The American Society for Pharmacology and Experimental Therapeutics.

Mhaouty-Kodja, S., et al., *Constitutively Active Alpha-1b Adrenergic Receptor Mutants Display Different Phosphorylation and Internalization Features*, Molecular Pharmacology, vol. 55, No. 2, Feb. 1999, pp. 339-347, The American Society for Pharmacology and Experimental Therapeutics.

Morise, H., et al., *Intermolecular Energy Transfer in the Bioluminescent System of Aequorea*, Biochemistry, vol. 13, No. 12, pp. 2656-2662, 1974.

Naga Prasad, S.V., et al., *Gβγ-dependent Phosphoinositide 3-Kinase Activation in Hearts with in Vivo Pressure Overload Hypertrophy*, Journal of Biological Chemistry, vol. 275, No. 7, Feb. 18, 2000, pp. 4693-4698.

Nelson, S., et al., *Characterization of an Intrinsically Fluorescent Gonadotropin-Releasing Hormone Receptor and Effects of Ligand Binding on Receptor Lateral Diffusion*, Endocrinology, vol. 140, No. 2, 1999, pp. 950-957, The Endocrine Society,USA.

Nestler, E.J., *Under Siege: The Brain on Opiates*, Neuron, vol. 16, pp. 897-900,May 1996, Cell Press.

Neuwald, A.F. et al., *HEAT Repeats associated with Condensins, Cohesins, and Other Complexes Involved in Chromosome Related Functions*, Genome Research, Cold Spring Laboratory Press, vol. 10, 2000, pp. 1445-1452.

Oakley, R.H., et al., *Differential Affinities of Visual Arrestin, β-Arrestin1, and β-Arrestin2 for G Protein-coupled Receptors Delineate Two Major Classes of Receptors*, published Mar. 29, 2000, JBC Papers in Press, and Journal of Biological Chemistry, vol. 275, No. 22, Jun. 2, 2000, pp. 17201-17210, The American Society for Biochemistry and Molecular Biology, Inc., USA.

Oakley, R.H., et al.,*Association of β-Arrestin with G Protein-coupled Receptors during Clathrin-mediated Endocytosis Dictates the Profile of Receptor Resensitization*, Journal of Biological Chemistry, vol. 274, No. 45, Nov. 5, 1999, pp. 32248-32257, The American Society for Biochemistry and Molecular Biology, Inc., USA.

Olson, K.R. et al., *Analysis of MAP 4 Function in Living Cells Using Green Fluorescent Protein (GFP) Chimeras*, Journal of Cell Biology, 1995,vol. 130, No. 3, pp. 639-650, The Rockefeller University Press.

Pisegna, J.R., et al., *Molecular Cloning of the Human Brain and Gastric Cholecystokinin Receptor: Structure, Functional Expression and Chromosomal Localization*, Biochemical And Biophysical Research Communications, vol. 189, No. 1, Nov. 30, 1992, pp. 296-303, Academic Press, USA.

Pitcher, J.A., et al., *G Protein-coupled Receptor Kinases*, Annual Review of Biochemistry, vol. 67, 1998, pp. 653-692, Annual Reviews, USA.

Probst, W.C., et al., *Sequence Alignment of the G-Protein Coupled Receptor Superfamily*, DNA and Cell Biology, vol. 11, No. 1, Jan. & Feb. 1992, pp. 1-20, Mary Ann Liebert, Inc. Publishers.

Rehfeld, J.F., et al., *Structure of the Bioactive Gastrins*, Chapter 1, 1993, pp. 1-14, Gastrin, Raven Press, New York, USA.

Rehfeld, J.F., *The New Biology of Gastrointestinal Hormones*, Physiological Reviews, vol. 78, No. 4, Oct. 1998, pp. 1087-1108, The American Physiological Society, USA.

Sadeghi, H.M., et al., *Maturation of Receptor Proteins in Eukaryotic Expression Systems*, Journal of Receptor & Signal Transduction Research, vol. 17, No. 1-3, 1997, pp. 433-445, Marcel Dekker, Inc., USA.

Sadeghi, H., et al., *O-Glycosylation of the V2 vasopressin receptor*, Glycobiology, vol. 9, No. 7, pp. 731-737, 1999, Oxford University Press, Printed by the Sheridan Press, USA.

Schöneberg, T., et al., *Functional rescue of mutant V2 vasopressin receptors causing nephrogenic diabetes insipidus by a co-expressed receptor polypeptide*, Embo Journal, vol. 15, No. 6, pp. 1283-1291, 1996, Oxford University Press.

Schöneberg, T., et al., *V2 Vasopressin Receptor Dysfunction in Nephrogenic Diabetes Insipidus Caused by Different Molecular Mechanisms*, Human Mutation, vol. 12, No. 3, pp. 196-205, 1998, Wiley-Liss, Inc.

Schulz, Rüdiger, et al., *Phosducin, β -arrestin and Opioid receptor migration*, European Journal of Pharmacology, vol. 375, No. 1-3, Jun. 30, 1999, pp. 349-357, Elsevier Science B.V.

Shi, W., et al., *Rhodopsin Arginine-135 Mutants Are Phosphorylated by Rhodopsin Kinase and Bind Arrestin in the Absence of 11-cis-Retinal*, Biochemistry, vol. 37, pp. 4869-4874, 1998, American Chemical Society, Washington, D.C.

Shetzline, M.A., et al., *A Role for Receptor Kinases in the Regulation of Class II G Protein-coupled Receptors: Phosphorylation and Desensitization of the Secretin Receptor*, Journal of Biological Chemistry, vol. 273, No. 12, Mar. 20, 1998, pp. 6756-6762, The American Society for Biochemistry and Molecular Biology, Inc., USA.

Sloas, D.D., et al., *A Nongastrin Malignant Ampullary Tumor Causing Gastric Acid and Pepsin Hypersecretion*, J. Clin Gastroenterol, vol. 12(5), 1990, pp. 573-578, Raven Press, Ltd., New York, USA.

Smith, A.J., et al., *CCK-B Receptor-Mediated Stimulation of Polyphosphoinositide Turnover in $GH_3$ Pituitary Cells in Response to Cholecystokinin and Pentagastrin*, Life Sciences, vol. 58, No. 11, 1996, pp. 883-895, Elsevier Science Inc., USA.

Sterne-Marr, R., et al., *Regulation of G Protein-coupled Receptors by Receptor Kinases and Arrestins*, Vitamins and Hormones, vol. 51, 1995, pp. 193-234, Academic Press, Inc.

Sternini, Catia, et al., *Agonist-selective endocytosis of μ opiod receptor by neurons in vivo*, Proceedings of the National Academy of Sciences USA, vol. 93, pp. 9241-9246 (Aug. 1996).

Tucker, J., et al., *Purification of a rat neurotensin receptor expressed in Escherichia coli*, Biochem, J, vol. 317, 1996, pp. 891-899, Printed in Great Britain.

Valette, F., et al.,*Construction of mutant and chimeric genes using the polymerase chain reaction*, Nucleic Acids Research, vol. 17, No. 2, pp. 723-733, 1989, IRL Press.

Van Solinge, W.W., et al., *Radioimmunoassey for Sequence 38-54 of Human Progastrin: Increased Diagnostic Specificity of Gastrin-Cell Disease*, Clinica Chimica Acta, vol. 192, 1990, pp. 35-46, Elsevier Science Publishers B.V.

Walker, J.K.L., et al., *Properties of Secretin Receptor Internalization Differ from Those of the $β_2$Adrenergic Receptor*, Journal of Biological Chemistry, vol. 274, No. 44, Oct. 29, 1999, pp. 31515-31523, The American Society for Biochemistry and Molecular Biology, Inc., USA.

Wank, S.A., *Cholecystokinin Receptors*, Am. J. Physiol, vol. 269, 1995, pp. G628-646.

Wank, S.A., et al., *Brain and Gastrointestinal Cholecystokinin Receptor Family: Structure and Functional Expression*, Proceedings of the National Academy of Sciences, vol. 89, Sep. 1992, pp. 8691-8695, Proc. Natl. Acad. Sci, USA.

Ward, W.W., et al., *Spectrophotometric Identity of the Energy Transfer Chromophores in Renilla and Aequorea Green-Fluorescent Proteins*, Photochemistry and Photobiology, 1980, vol. 31, pp. 611-615, Pergamon Press, Ltd., Great Britain.

Whistler, Jennifer, L., et al., *Morphine-activated opioid receptors elude desensitization by β-arrestin*, Proceedings of the National Academy of Sciences of the United States, vol. 95, No. 17, Aug. 18, 1998, pp. 9914-9919.

Wolfe, M.M., et al., *Zollinger-Ellison Syndrome Associated with Persistently Normal Fasting Serum Gastrin Concentrations*, Annals of Internal Medicine, vol. 103, 1985, pp. 215-217, USA.

Wolfe, M.M., et al., *Zollinger-Ellison Syndrome, Current Concepts in Diagnosis and Management*, New England Journal of Medicine, vol. 317, Nov. 5, 1987, pp. 1200-1209, USA.

Yu, Yunkai, et al., *μ Opiod Receptor Phosphorylation, Desensitization, and Ligand Efficacy*, Journal of Biological Chemistry, vol. 272, No. 46, pp. 28869-28874 (1997).

Zhang, J., et al., *Cellular Trafficking of G Protein-coupled Receptor/ β-Arrestin Endocytic Complexes*, Journal of Biological Chemistry, vol. 274, No. 16, Apr. 16, 1999, pp. 10999-11006, The American Society for Biochemistry and Molecular Biology, Inc., USA.

Zhang, J. et al., *Role for G protein-coupled receptor kinase in agonist-specific regulation of μ-opiod receptor responsiveness*, Proceedings of the National Academy of Sciences, USA, vol. 95, pp. 7157-7162 (Jun. 1998).

Zhang, J., et al., *A Central Role for β-Arrestins and Clathrin-coated Vesicle-mediated Endocytosis in β$_2$-Adrenergic Receptor Resensitization*, Journal of Biological Chemistry, vol. 272, No. 43, Oct. 24, 1997, pp. 27005-27014, The American Society for Biochemistry and Molecular Biology, Inc., USA.

Zhang, J., et al., *Dynamin and β-Arrestin Reveal Distinct Mechanisms for G Protein-coupled Receptor Internalization*, Journal of Biological Chemistry, vol. 271, No. 31, pp. 18302-18305, 1996, USA.

Zimmer, T., et al., *Brief Report: A Duodenal Gastrinoma in a Patient with Diarrhea and Normal Serum Gastrin Concentrations*, New England Journal of Medicine, vol. 333, Sep. 7, 1995, pp. 634-636, USA.

Barak, L., et al., *Internal Trafficking and Surface Mobility of a Funtionally Intact β$_2$-Adrenergic Receptor-Green Fluorescent Protein Conjugate*, Mole Pharm. 51:177-184 (1997).

Barak, L., et al., *The Conserved Seven-Transmembrane Sequence $NP(X)_{2,3}$ Y of the G-Protein-Coupled Receptor Superfamily Regulates Multiple Properties of the β$_2$-Adrenergic Receptor*, Biochem. 3415407-15414 (1995).

Barak, L, et al., *A Highly Conserved Tyrosine Residue in G Protein-coupled Receptors is Required for Agonist-mediated β$_2$-Adrenergic Receptor*, J. of Biological Chem. 269, No. 42790-2795 (1994).

Ferguson, S., et al., *Role of Phosphorylation in Agonist-promoted β$_2$-Adrenergic Receptor Sequestration*, The J. Of Biological Chem. 270, No. 42:24782-24789 (1995).

Ferguson, S., et al., *Role of β-Arrestin in Mediating Agonist-Promoted G Protein-Coupled Receptor Internalization*, Science 271:363-366 (1996).

Lohse, M., et al., *β-Arrestin: A Protein That Regulates β-Adrenergic Receptor Function*, Science 248:1547-1550 (1990).

Mènard, L., et al., *Members of the G Protein-Coupled Receptor Kinase Family That Phosphorylate the β-Adrenergic Receptor Facilitate Sequestration*, Biochem. 35:4155-4160 (1996).

Ormö, M., et al., *Crystal Structure of the Aequorea victoria Green Fluorescent Proteins*, Science 273:1392-1395 (1996).

Cubitt, A., et al., *Understanding, Improving and Using Green Fluorescent Proteins*, Trends in Biochemical Sciences, 448-455 (1995).

Harris, E., et al, *Protein Purification Methods*, Oxford University Press, New York, 12-18, (1990).

Yokoe, *Spatial Dynamics of GFP-tagged proteins investigated by local fluorescence enhancement*, Nature Biotechnology, 14:1252 (Oct. 1996).

Barak, et al., *Abstract #2484*, Molecular Biology of the Cell, 7:427a (Dec. 1996).

Attramadal, et al., *β-Arrestin2, a Novel Member of the Arrestin/β-Arrestin Gene Family**, The Journal of Biological Chemistry, 267:25 17882-17890 (1992).

Barak, et al., *A β-Arrestin/Green Fluorescent Protein Biosensor for Detecting G Protein-coupled Receptor Activation**, The Journal of Biological Chemistry, 272:44 27497-27500 (1997).

Ferguson, et al., *Molecular Mechanisms of G Protein-Coupled Receptor Desensitization and Resensitization*, Life Sciences, 62:17/18 1561-1565 (1998).

Heim, Roger, et al., "Wavelength mutations and posttranslational autoxidation of green fluorescent protein," Proceedings of the National Academy of Sciences, USA, Dec. 20, 1994, pp. 12501-12504, vol. 91, No. 26, Academy of Sciences of the United States.

Prasher, Douglas C., et al., "Primary structure of the *Aequorea victoria* green-fluorescent protein," Gene, 1992, vol. 111, pp. 229-233, No. 2, Elsevier Science Publishers B.V.

Goodman, O., et al., "β-Arrestin acts as a clathrin adaptor in endocytosis of the β$_2$-Adrenergic receptor", Nature, 383(3):447-450, 1996.

McConalogue, K, et al., "Cellular and Subcellular Localization of G-Protein Receptor Kinases, Arrestins and G-Proteins: Implications for Receptor Regulation", Gastroenterology, 110(4): 1 Supplement:A1098 AGA Abstracts, 1996..

Zuckerman, R. and Cheasty, J. E., "Sites of arrestin action during the quench phenomenon in retinal rods", Febs. Let., [Elsevier] 238(2): 379-384, 1988.

* cited by examiner

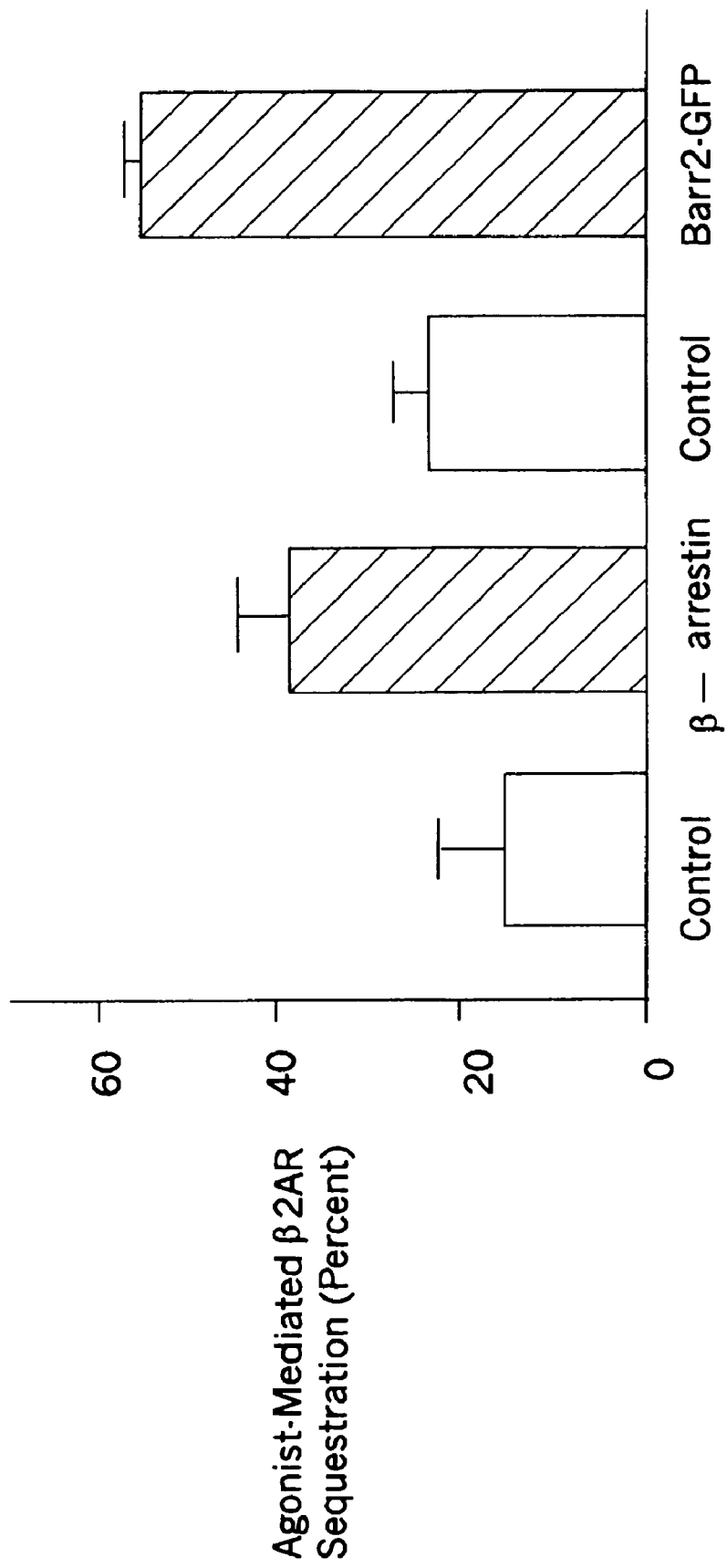

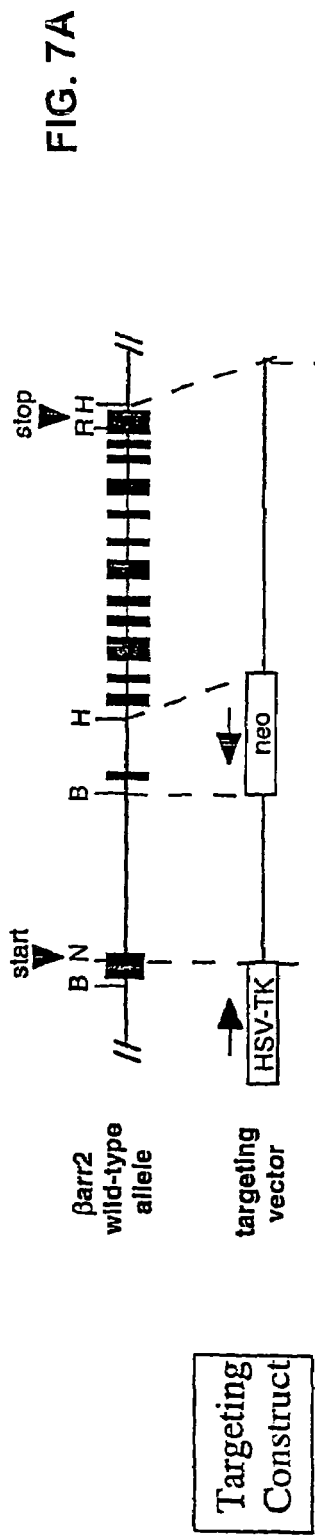
FIG. 7A
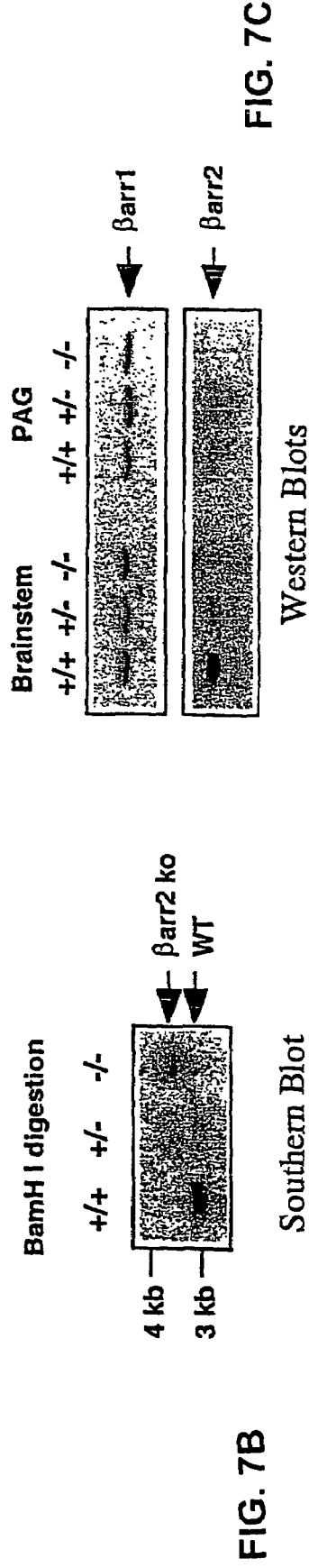
FIG. 7C
FIG. 7B

Hotplate (56°C, 30 sec cutoff) paw-withdrawal latency after morphine (30 min, s.c.) and naloxone (2.5 mg/kg, 10 min, s.c.).

[35S]GTPγS Binding in Periaqueductal Gray Membranes

US 7,572,888 B2

METHODS OF ASSAYING RECEPTOR ACTIVITY AND CONSTRUCTS USEFUL IN SUCH METHODS

This application is a continuation of application Ser. No. 09/772,644 filed Jan. 30, 2001, now U.S. Pat. No. 6,770,449 entitled Methods of Assaying Receptor Activity and Constructs Useful in Such Methods; which is a continuation of application Ser. No. 09/469,554 filed Dec. 22, 1999, now U.S. Pat. No. 6,528,271 entitled Inhibition of β-arrestin Mediated Effects Prolongs and Potentiates Opioid Receptor-Mediated Analgesia; which is a continuation in part of Ser. No. 09/233,530, filed Jan. 20, 1999, entitled Methods of Assaying Receptor Activity and Constructs Useful in Such Methods, now U.S. Pat. No. 6,110,693, issued Aug. 29, 2000; which is a continuation of Ser. No. 08/869,568, filed Jun. 5, 1997, entitled Methods of Assaying Receptor Activity and Constructs Useful in Such Methods, now U.S. Pat. No. 5,891,646, issued Apr. 6, 1999, the contents of which are hereby incorporated by reference in their entireties.

FEDERALLY SPONSORED RESEARCH

This invention was made with Government support under National Institutes of Health Grant No. HL 03422-02, HL 16037, and NS 19576. The Government has certain rights to this invention.

FIELD OF THE INVENTION

This invention relates to methods of detecting G-protein coupled receptor (GPCR)activity in vivo and in vitro, and provides methods of assaying GPCR activity, and methods of screening for GPCR ligands, G protein-coupled receptor kinase (GRK) activity, and compounds that interact with components of the GPCR regulatory process. This invention also provides constructs useful in such methods.

BACKGROUND OF THE INVENTION

The actions of many extracellular signals are mediated by the interaction of G-protein coupled receptors (GPCRs) and guanine nucleotide-binding regulatory proteins (G proteins). G protein-mediated signaling systems have been identified in many divergent organisms, such as mammals and yeast. GPCRs respond to, among other extracellular signals, neurotransmitters, hormones, odorants and light. GPCRs are similar and possess a number of highly conserved amino acids; the GPCRs are thought to represent a large 'superfamily' of proteins. Individual GPCR types activate a particular signal transduction pathway; at least ten different signal transduction pathways are known to be activated via GPCRs. For example, the beta 2-adrenergic receptor (βAR) is a prototype mammalian GPCR. In response to agonist binding, βAR receptors activate a G protein ($G_s$) which in turn stimulates adenylate cyclase and cyclic adenosine monophosphate production in the cell.

It has been postulated that members of the GPCR superfamily desensitize via a common mechanism involving G protein-coupled receptor kinase (GRK) phosphorylation followed by arrestin binding. Gurevich et al., *J. Biol. Chem;* 270:720 (1995); Ferguson et al., *Can. J. Physiol. Pharmacol.* 74:1095 (1996). However, the localization and the source of the pool of arrestin molecules targeted to receptors in response to agonist activation was unknown. Moreover, except for a limited number of receptors, a common role for β-arrestin in GPCR desensitization had not been established. The role of β-arrestins in GPCR signal transduction was postulated primarily due to the biochemical observations.

Many available therapeutic drugs in use today target GPCRs, as they mediate vital physiological responses, including vasodilation, heart rate, bronchodilation, endocrine secretion, and gut peristalsis. See, eg., Lefkowitz et al., *Ann. Rev. Biochem.* 52:159 (1983). GPCRs include the adrenergic receptors (alpha and beta); ligands to beta ARs are used in the treatment of anaphylaxis, shock, hypertension, hypotension, asthma and other conditions. Additionally, spontaneous activation of GPCRs occurs, where a GPCR cellular response is generated in the absence of a ligand. Increased spontaneous activity can be decreased by antagonists of the GPCR (a process known as inverse agonism); such methods are therapeutically important where diseases cause an increase in spontaneous GPCR activity.

Efforts such as the Human Genome Project are identifying new GPCRs ('orphan' receptors) whose physiological roles and ligands are unknown. It is estimated that several thousand GPCRs exist in the human genome. With only about 10% of the human genome sequenced, 250 GPCRs have been identified; fewer than 150 have been associated with ligands.

SUMMARY OF THE INVENTION

A first aspect of the present invention is a conjugate of a β-arrestin protein and a detectable molecule. The detectable molecule may be an optically detectable molecule, such as Green Fluorescent Protein.

A further aspect of the present invention is a nucleic acid construct comprising an expression cassette. The construct includes, in the 5' to 3' direction, a promoter and a nucleic acid segment operatively associated with the promoter, and the nucleic acid segment encodes a β-arrestin protein and detectable molecule. The detectable molecule may be an optically detectable molecule such as Green Fluorescent Protein.

A further aspect of the present invention is a host cell containing a nucleic acid molecule which includes, a promoter operable in the host cell and a nucleic acid sequence encoding a β-arrestin protein and a detectable molecule. The detectable molecule may be an optically detectable molecule such as Green Fluorescent Protein. The cell may be a mammalian, bacterial, yeast, fungal, plant or animal cell, and may be deposited on a substrate.

A further aspect of the present invention is a method of assessing G protein coupled receptor (GPCR) pathway activity under test conditions, by providing a test cell that expresses a GPCR and that contains a conjugate of a β-arrestin protein and a visually detectable molecule; exposing the test cell to a known GPCR agonist under test conditions; and then detecting translocation of the detectable molecule from the cytosol of the test cell to the membrane edge of the test cell. Translocation of the detectable molecule in the test cell indicates activation of the GPCR pathway. Exemplary test conditions include the presence in the test cell of a test kinase and/or a test G-protein, or exposure of the test cell to a test ligand, or co-expression in the test cell of a second receptor.

A further aspect of the present invention is a method for screening a β-arrestin protein (or fragment of a β-arrestin protein) for the ability to bind to a phosphorylated GPCR. A cell is provided that expresses a GPCR and contains a conjugate of a test β-arrestin protein and a visually detectable molecule. The cell is exposed to a known GPCR agonist and then translocation of the detectable molecule from the cell cytosol to the cell edge is detected. Translocation of the detectable molecule indicates that the β-arrestin molecule can bind to phosphorylated GPCR in the test cell.

A further aspect of the present invention is a method to screen a test compound for G protein coupled receptor (GPCR) agonist activity. A test cell is provided that expresses a GPCR and contains a conjugate of a β-arrestin protein and a visually detectable molecule. The cell is exposed to a test compound, and translocation of the detectable molecule from the cell cytosol to the membrane edge is detected. Movement of the detectable molecule to the membrane edge after exposure of the cell to the test compound indicates GPCR agonist activity of the test compound. The test cell may express a known GPCR or a variety of known GPCRs, or express an unknown GPCR or a variety of unknown GPCRS. The GPCR may be, for example, an odorant GPCR or a β-adrenergic GPCR. The test cell may be a mammalian, bacterial, yeast, fungal, plant or animal cell.

A further aspect of the present invention is a method of screening a sample solution for the presence of an agonist to a G protein coupled receptor (GPCR). A test cell is provided that expresses a GPCR and contains a conjugate of a β-arrestin protein and a visually detectable molecule. The test cell is exposed to a sample solution, and translocation of the detectable molecule from the cell cytosol to the membrane edge is assessed. Movement of the detectable molecule to the membrane edge after exposure to the sample solution indicates the sample solution contains an agonist for a GPCR expressed in the cell.

A further aspect of the present invention is a method of screening a test compound for G protein coupled receptor (GPCR) antagonist activity. A cell is provided that expresses a GPCR and contains a conjugate of a β-arrestin protein and a visually detectable molecule. The cell is exposed to a test compound and to a GPCR agonist, and translocation of the detectable molecule from the cell cytosol to the membrane edge is detected. When exposure to the agonist occurs at the same time as or subsequent to exposure to the test compound, movement of the detectable molecule from the cytosol to the membrane edge after exposure to the test compound indicates that the test compound is not a GPCR antagonist.

A further aspect of the present invention is a method of screening a test compound for G protein coupled receptor (GPCR) antagonist activity. A test cell is provided that expresses a GPCR and contains a conjugate of a β-arrestin protein and a visually detectable molecule. The cell is exposed to a GPCR agonist so that translocation of the detectable molecule from the cytosol of the cell to the membrane edge of the cell occurs, and the cell is then exposed to a test compound. Where exposure to the agonist occurs prior to exposure to the test compound, movement of the detectable molecule from the membrane edge of the cell to the cytosol after exposure of the cell to the test compound indicates that the test compound has GPCR antagonist activity.

A further aspect of the present invention is a method of screening a cell for the presence of a G protein coupled receptor (GPCR). A test cell is provided that contains a conjugate of a β-arrestin protein and a visually detectable molecule. The test cell is exposed to a solution containing a GPCR agonist. Any translocation of the detectable molecule from the cytosol to the membrane edge is detected; movement of the detectable molecule from the cytosol to the membrane edge after exposure of the test cell to GPCR agonist indicates that the test cell contains a GPCR.

A further aspect of the present invention is a method of screening a plurality of cells for those cells which contain a G protein coupled receptor (GPCR). A plurality of test cells containing a conjugate of a β-arrestin protein and a visually detectable molecule are provided, and the test cells are exposed to a known GPCR agonist. Cells in which the detectable molecule is translocated from the cytosol to the membrane edge are identified or detected. Movement of the detectable molecule to the membrane edge after exposure to a GPCR agonist indicates that the cell contains a GPCR responsive to that GPCR agonist. The plurality of test cells may be contained in a tissue, an organ, or an intact animal.

A further aspect of the present invention is a substrate having deposited thereon a plurality of cells that express a GPCR and that contain a conjugate of β-arrestin protein and a detectable molecule. Such substrates may be made of glass, plastic, ceramic, semiconductor, silica, fiber optic, diamond, biocompatible monomer, or biocompatible polymer materials.

A further aspect of the present invention is an apparatus for determining GPCR activity in a test cell. The apparatus includes means for measuring indicia of the intracellular distribution of a detectable molecule, and a computer program product that includes a computer readable storage medium having computer-readable program code means embodied in the medium. The computer-readable program code means includes computer-readable program code means for determining whether the indicia of the distribution of the detectable molecule in a test cell indicates concentration of the detectable molecule at the cell membrane, based on comparison to the measured indicia of the intracellular distribution of a detectable molecule in a control cell. The indicia of the intracellular distribution of the detectable molecule may be optical indicia, and the measuring means may be means for measuring fluorescent intensity. The molecule to be detected may be one that is fluorescently detectable, and the step of measuring the indicia of the intracellular distribution of the detectable molecule may include measurement of fluorescence signals from test and control cells.

A further aspect of the present invention is an apparatus for determining GPCR activity in a test cell. The apparatus includes means for measuring indicia of the intracellular distribution of a detectable molecule in at least one test cell at multiple time points, and a computer program product. The computer program product includes a computer readable storage medium having computer-readable program code means embodied in said medium. The computer-readable program code means includes computer-readable program code means for determining whether the indicia of the distribution of the detectable molecule in the test cell at multiple time points indicates translocation of the detectable molecule to the cell membrane.

A further aspect of the present invention is an apparatus for determining GPCR activity in a test cell, which includes means for measuring indicia of the intracellular distribution of a detectable molecule in at least one test cell, and a computer program product. The computer program product includes a computer readable storage medium having computer-readable program code means embodied therein and including computer-readable program code means for determining whether the indicia of the distribution of the detectable molecule in the test cell indicates concentration of the detectable molecule at the cell membrane, based on comparison to pre-established criteria.

Pain perception (nociception) is mediated by a cascade of events from the point of the stimulus to integrative circuits in the brain. Nociception involves signals that are mediated by several classes of receptors and signal transduction mechanisms such as GPCRs for substance P, opioid peptides, etc. and ion channels such as NMDA receptors. Antinociception has been known for more than 1000 years to be induced by the alkaloid compound, morphine, which functions as an agonist at the μ opioid receptor. The activity of agonists for signaling through GPCRs is usually limited by cellular mechanisms that dampen the signal of the agonist, a process referred to as desensitization. These mechanisms include phosphorylation of agonist-activated receptors by specific receptor kinases called GRKs followed by the interaction of the phosphorylated GPCR with any of the members of the arrestin family of proteins. Morphine-mediated antinociception is known to wane with time, however the contribution of the desensitization is controversial and for all practical purposes is unknown. With the βarrestin knockout mice disclosed herein, it is shown that interfering with (eliminating) one of the key protein components of the desensitization mechanism greatly enhances the potency and efficacy of the antinociceptive properties of morphine.

Accordingly, an additional aspect of the present invention is a knockout mouse useful for testing the efficacy of potential analgesic agents, the cells of said mouse containing at least one inactive endogenous βarrestin gene (preferably the βarrestin-2 gene), the mouse exhibiting a phenotype of decreased sensitivity to pain after administration of a μ opioid receptor agonist such as morphine as compared to the corresponding wild type mouse. The mouse may be heterozygous or homozygous for the inactive endogenous βarrestin gene. The mouse is useful for evaluating potential analgesic drugs, and particularly for evaluating the contribution of the desensitization mechanisms to the antinociceptive effects of endogenous opioids.

BRIEF DESCRIPTION OF THE DRAWINGS

FIG. 2B shows the sequestration of β2AR in COS cells with and without overexpressed β-arrestin2 (left two bars) and with and without overexpressed βarr2-GFP (right two bars). Wild type β-arrestin2 and βarr2-GFP enhanced β2AR sequestration equally well above control levels, producing a 2.5 and 2.4 fold increase, respectively.

FIG. 4 depicts a HEK-293 cell containing 12CA5(HA) tagged β2AR (confocal microscopic photographs).

FIG. 7 illustrates characteristics of the targeted disruption of the mouse βarrestin-2 (βarr2) gene.

FIG. 7A depicts schematic diagrams of βarr2 gene (top), targeting vector (middle) and the homologous recombinant gene (bottom) (7). The arrows indicate the translational start and stop sites. The black boxes indicate the exons. A 0.8 kb Bam HI-Hind III fragment was replaced with the pGK-neo cassette such that the entire exon 2, encoding amino acids 9-19, was deleted. Transcription of the neomycinresistant gene opposed that of the βarr2 gene. Both 5' and 3' external probes were used in genotype screening. Restriction enzyme sites are as follows: B, Bam HI; N, Nco 1; H, Hind III; R, Eco RI.

FIG. 7B illustrates southern blot analysis of genomic DNA from wild type (WT), heterozygous (+/−) and homozygous (−/−) mice. Tail DNA was digested with Bam HI and analyzed by Southern blotting with the 5' probe as shown in (A). A 3.5-kb fragment is indicative of the βarr2 knock-out (KO) allele and a 3-kb fragment is indicative of the wild-type allele.

FIG. 7C depicts protein immunoblot analysis of βarr2 expression in WT, βarr2 and βarr2-KO mice. Membranes were blotted for βarr (top) and βarr2 (bottom) protein expression. Each lane was loaded with 25 pLg protein derived from the same lysates of the indicated brain regions.

DETAILED DESCRIPTION OF THE INVENTION

Definitions

Figure 1:
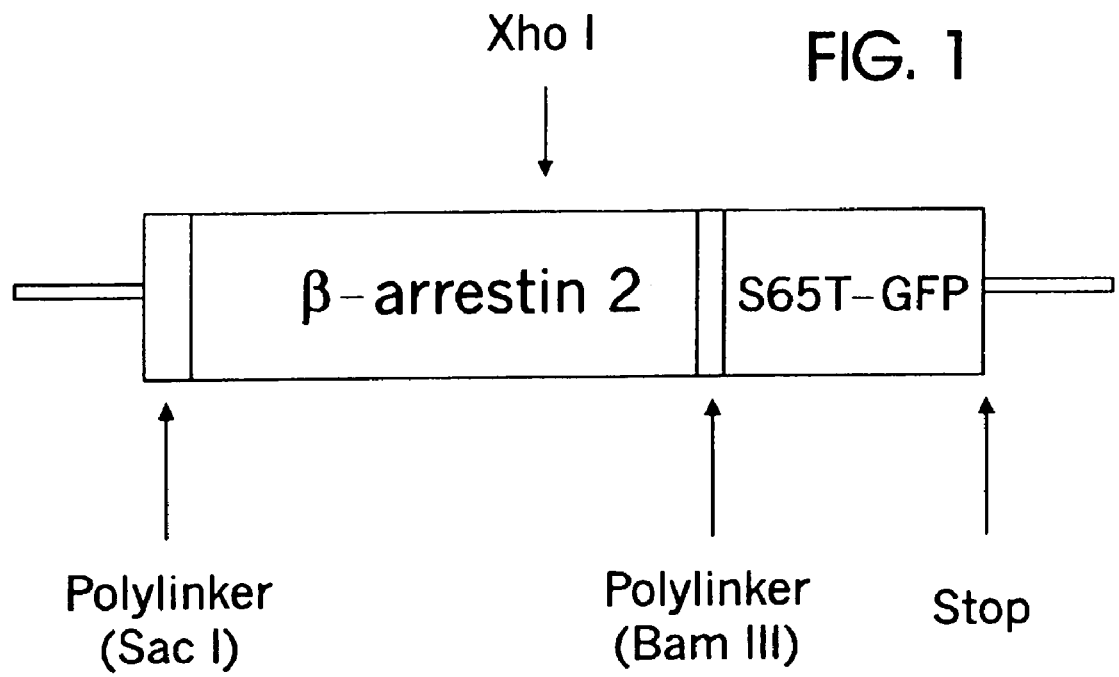
FIG. 1 is a linear model of the β-arrestin2/S65T-Green Fluorescent Protein (GFP) conjugate.

The term "arrestin" as used herein has its ordinary meaning in the art and is intended to encompass all types of arrestin, including but not limited to visual arrestin (sometimes referred to as Arrestin 1), βarrestin 1 (sometimes referred to as Arrestin 2), and βarrestin 2 (sometimes referred to as Arrestin 3).

The term "βarrestin" (or "βarrestin") as used herein is intended to encompass all types of βarrestin, including but not limited to βarrestin 1 and βarrestin 2.

The phrases "concurrent administration," "administration in combination, if "simultaneous administration" or "administered simultaneously" as used herein, interchangeably mean that the compounds are administered at the same point in time or immediately following one another. In the latter case, the two compounds are administered at times sufficiently close that the results observed are indistinguishable from those achieved when the compounds are administered at the same point in time.

As used herein, exogenous or heterologous DNA (or RNA) refers to DNA (or RNA) which has been introduced into a cell (or the cell's ancestor) through the efforts of humans. Such heterologous DNA may be a copy of a sequence which is naturally found in the cell being transformed, or a sequence which is not naturally found in the cell being transformed, or fragments thereof.

As used herein, the term 'gene' refers to a DNA sequence that incorporates (1) upstream (5') regulatory signals including a promoter, (2) a coding region specifying the product, protein or RNA of the gene, (3) downstream (3') regions including transcription termination and polyadenylation signals and (4) associated sequences required for efficient and specific expression.

Use of the phrase "substantial sequence similarity" in the present specification refers to DNA, RNA or amino acid sequences which have slight and non-consequential sequence variations from a sequence of interest, and are considered to be equivalent to the sequence of interest. In this regard, "slight and non-consequential sequence variations" mean that "similar" sequences (i.e., sequences that have substantial sequence similarity) will be functionally equivalent. Functionally equivalent sequences will function in substantially the same manner to produce substantially the same compositions.

As used herein, a "native DNA sequence" or "natural DNA sequence" means a DNA sequence which can be isolated from non-transgenic cells or tissue. Native DNA sequences are those which have not been artificially altered, such as by site-directed mutagenesis. Once native DNA sequences are identified, DNA molecules having native DNA sequences may be chemically synthesized or produced using recombinant DNA procedures as are known in the art.

As used herein, "a regulatory element" from a gene is the DNA sequence which is necessary for the expression of the gene, such as a promoter. In this invention, the term "operatively linked" to means that following such a link a regulatory element can direct the expression of a linked DNA sequence.

The term 'promoter' refers to a region of a DNA sequence that incorporates the necessary signals for the efficient expression of a coding sequence. This may include sequences to which an RNA polymerase binds but is not limited to such sequences and may include regions to which other regulatory proteins bind together with regions involved in the control of protein translation and may include coding sequences. Suitable promoters will be apparent to those skilled in the art, and will vary depending upon the cell in which the DNA is to be expressed. A suitable promoter for use in DNA constructs encoding a βarrestin/detectable molecule construct may be a promoter naturally found in the cell in which expression is desired; optionally, the promoter of the βarrestin within the construct may be utilized. Both inducible and constitutive promoters are contemplated for use in the present invention.

DNA Constructs

DNA constructs, or "expression cassettes," of the present invention include, 5' to 3' in the direction of transcription, a promoter, a DNA sequence operatively associated with the promoter, and, optionally, a termination sequence including stop signal for RNA polymerase and a polyadenylation signal for polyadenylase. All of these regulatory regions should be capable of operating in the cell to be transformed. Suitable termination signals for a given DNA construct will be apparent to those of skill in the art.

The term "operatively associated," as used herein, refers to DNA sequences on a single DNA molecule which are associated so that the function of one is affected by the other. Thus, a promoter is operatively associated with a DNA when it is capable of affecting the transcription of that DNA (i.e., the DNA is under the transcriptional control of the promoter). The promoter is said to be "upstream" from the DNA, which is in turn said to be "downstream" from the promoter.

The present inventors have determined that βarrestin redistribution from the cytosol to the plasma membrane occurs in response to agonist activation of GPCRs. The present inventors demonstrated a common role for βarrestin in agonist-mediated signal transduction termination following agonist activation of receptors. The present inventors have devised convenient methods of assaying agonist stimulation of GPCRS in vivo and in vitro in real time. Although the pharmacology of members of the GPCR superfamily differs, the methods of the present invention utilize βarrestin translocation to provide a single-step, real-time assessment of GPCR function for multiple, distinct members of the GPCR superfamily. The present methods may additionally be utilized in studying and understanding the mechanisms of actions of various therapeutic agents. The present inventors have determined that a protein conjugate or chimera comprising an arrestin molecule and a detectable molecule (such as Green Fluorescent Protein) is useful in such methods of assaying in vivo GPCR activity.

Due to the therapeutic importance of GPCRs, methods for the rapid screening of compounds for GPCR ligand activity are desirable. Additionally, methods of screening orphan GPCRs for interactions with known and putative GPCR ligands assist in characterizing such receptors. Optical methods are available for studying labelled protein dynamics in intact cells, including video microscopy, fluorescence recovery after photobleaching, and resonance energy transfer. However, such methods are of limited usefulness in labeling GPCRs for study, due to the relatively low level of GPCR expression and the alterations in receptor function that can occur after tagging or labeling of the receptor protein. Radiolabeling or fluorescent labeling of test ligands has also been utilized in screening for GPCR ligands. See, e.g. Atlas et al., Proc. Natl. Acad. Sci. USA 74:5490 (1977); U.S. Pat. No. 5,576,436 to McCabe et al. (all patents cited herein are incorporated herein in their entirety). The introduction of foreign epitopes into receptor cDNA to produce hybrid GPCRs is now a standard technique, and enhances detection of GPCRs by monoclonal antibody technology. However, such techniques are limited in their applicability to living cells. U.S. Pat. No. 5,284,746 to Sledziewski describes yeast-mammalian hybrid GPCRs and methods of screening for GPCR ligands using such hybrid receptors. U.S. Pat. No. 5,482,835 to King et al. describes methods of testing in yeast cells for ligands of mammalian GPCRs. However, application of these techniques to the study or identification of orphan GPCRs requires prior knowledge of ligands or signal transduction events and are therefor not generally applicable or universal.

Phosphorylation of GPCRs is a mechanism leading to desensitization of the receptors; receptors that have been continuously or repeatedly stimulated lose responsiveness, whereas the responses of other receptors remain intact. See Harden, Pharmacol. Rev. 35:5 (1983); Benovic et al., Annu. Rev. Cell. Biol. 4:405(1988). In a variety of cells, specific kinases have evolved for specific GPCRs. Desensitization occurs via the following pathway: agonist occupancy of the receptor transforms the receptor into an appropriate substrate for an associated kinase; βarrestin binds to the kinase phosphorylated receptor and prevents subsequent interaction with the appropriate G-protein, as well as initiating both internalization and resensitization processes. Ferguson et al, Science, 271:363 (1996); Lohse et al., Science 248:1547 (1990). βarrestin dependent desensitization is induced only when the GPCR is activated by ligand binding, and is an example of homologous desensitization (i.e., the ligand desensitizes only its target receptors). Lohse et al. (1990) and Attramadal et al., J. Biol. Chem. 267:17882 (1992) provide cDNA and amino acid sequences of βarrestin. Various isoforms of βarrestin are known; as used herein, βarrestin refers to all such isoforms of βarrestin, proteins having substantial sequence similarity thereto which are functional βarrestins, and functional fragments thereof. Functional fragments of βarrestin, its isoforms and analogs, may be determined using techniques as known in the art.

Molecules detectable by spectroscopic, photochemical, biochemical, immunochemical, electrical and optical means are known. Optically detectable molecules include fluorescent labels, such as commercially available fluorescein and Texas Red. Detectable molecules useful in the present invention include any biologically compatible molecule which may be conjugated to a βarrestin protein without compromising the ability of βarrestin to interact with the GPCR system, and without compromising the ability of the detectable molecule to be detected. Conjugated molecules (or conjugates) of βarrestin and detectable molecules (which also may be termed 'detectably labelled βarrestins') are thus useful in the present invention. Preferred are detectable molecules capable of being synthesized in the cell to be studied (e.g., where the cell can be transformed with heterologous DNA so that the βarrestin-detectable molecule chimera is produced within the cell). Particularly preferred are those detectable molecules which are inherently fluorescent in vivo. Suitable detectable molecules must be able to be detected with sufficient resolution within a cell that translocation of βarrestin from the cytosol to the cell membrane in response to agonist binding to GPCR can be qualitatively or quantitatively assessed. Molecules detectable by optical means are presently preferred.

Fusion proteins with coding sequences for β-galactosidase, firefly luciferase, and bacterial luciferase have been used in methods of detecting gene expression and protein interactions in cells. However, these methods require exogenously-added substrates or cofactors. In the methods of the present invention, an inherently fluorescent marker molecule is preferred, such as GFP, since detection of such a marker intracellularly requires only the radiation by the appropriate wavelength of light and is not substrate limited.

Green Fluorescent Protein (GFP) was first isolated from the jelly fish *Aequorea victoria*, and has an inherent green bioluminescence that can be excited optically by blue light or nonradiative energy transfer. Sequences of GFP-encoding cDNA and GFP proteins are known; see, e.g., Prasher et al., Gene, 111:229 (1992). The crystalline structure of GFP is described in Ormo et al., Science 273:1392 (1996). Purified native GFP absorbs blue light (maximally at 395 nm with a minor peak at 470 m) and emits green light (peak emission at 509 nm) (Morise et al, *Biochemistry,* 13:2656 (1974); Ward et al., *Photochem. Photobiol.,* 31:611 (1980)). It has been shown that GFP expressed in prokaryotic and eukaryotic cells produces a strong green fluorescence when excited by near UV or blue light (see U.S. Pat. No. 5,491,084 to Chalfie and Prasher); as this fluorescence requires no additional gene products from *A. victoria,* chromophore formation is not species specific and occurs either through the uses of ubiquitous cellular components or by autocatalysis. Expression of GFP in *Escherichia coli* results in an easily detected green fluorescence that is not seen in control bacteria. See Chalfie et al., *Science* 263:802 (1994); U.S. Pat. No. 5,491,084. Cells expressing the green-fluorescent proteins may be conveniently separated from those which do not express the protein by a fluorescence-activated cell sorter.

As used herein, Green Fluorescent Protein refers to the various naturally occurring forms of GFP which can be isolated from natural sources, as well as artificially modified GFPs which retain the fluorescent abilities of native GFP. As discussed in Ormo et al., *Science* 273:1392 (1996), various mutants of GFP have been created with altered excitation and emission maxima. Two characteristics of wild-type GFP which affect its usefulness in mammalian cell lines are the need to excite it at UV wavelengths to obtain a maximal fluorescent signal, and decreased fluorescence at temperatures over 23.degree. C. However, the S65T/GFP mutant overcomes these limitations. Heim et al., *Proc. Natl. Acad. Sci. USA* 91:12501 (1994). Additional alterations in the GFP protein sequence which provide inherently fluorescent, biologically compatible molecules will be apparent to those in the art; sequence alterations may be made to alter the solubility characteristics of the protein, its excitation wavelength, or other characteristics, while retaining useful fluorescent properties. See, e.g. U.S. Pat. No. 5,625,048 to Tsien and Heim; WO 9711091 (Bjorn, Poulsen, Thastrup and Tullin); WO 9627675 (Haseloff, Hodge, Prasher and Siemering); WO 9627027 (Ward); WO 9623898 (Bjorn et al.); WO 9623810 (Heim and Tsien); WO 9521191 (Chalfie and Ward).

Cells useful in the methods of the present invention include eukaryotic and prokaryotic cells, including but not limited to bacterial cells, yeast cells, fungal cells, insect cells, nematode cells, plant or animal cells. Suitable animal cells include, but are not limited to HEK cells, HeLa cells, COS cells, and various primary mammalian cells. Cells contained in intact animals, including but not limited to nematodes, zebrafish (and other transparent or semi-transparent animals) and fruitflies, may also be used in the methods of the present invention. An animal model expressing a β-arrestin-detectable molecule fusion protein throughout its tissues, or within a particular organ or tissue type, will be useful in studying cellular targets of known or unknown GPCR ligands.

Cells useful in the present methods include those which express a known GPCR or a variety of known GPCRs, or which express an unknown GPCR or a variety of unknown GPCRs. As used herein, a cell which expresses a GPCR is one which contains that GPCR as a functional receptor in its membrane; the cells may naturally express the GPCR(s) of interest, or may be genetically engineered to express the GPCR(s) of interest. As used herein, an 'unknown' or 'orphan' receptor is one whose function is unknown, and/or whose ligands are unknown.

The Present Experiments

Green fluorescent protein (GFP) has been used to study protein-protein interactions in living cells. See Kaether & Gerdes, *FEBS Lett.* 369:267 (1995); Olson et al., *J. Cell. Biol.* 130:639 (1995). Green fluorescent protein (GFP) is useful as a reporter molecule for fusion proteins due to its inherent fluorescence and its folding, which apparently isolates it from its conjugated partner. Prasher et al., *Gene* 111:229 (1992); Ormo et al., *Science* 273:1392 (1996). For example, a seven transmembrane protein as complex as the β2AR, which is three times larger than GFP, exhibits normal biochemistry after GFP conjugation to its C-terminus. Barak et al., *Mol. Pharmacol.* 51:177 (1997).

The present inventors established that a fusion protein consisting of a β-arrestin molecule (β-arrestin2) conjugated to a GFP at its C-terminus (βarr2-GFP, FIG. 1) is expressed in cells and is biologically active. The βarr2-GFP fusion protein is approximately 50% larger than β-arrestin2, and this size increase is reflected by its slower migration on SDS-Page (FIG. 2A). The left lane of FIG. 2A, exposed to an antibody against β-arrestin, shows that βarr2-GFP runs more slowly than endogenous β-arrestin2 (highlighted middle band). The right lane of FIG. 2A, treated with a monoclonal anti-GFP antibody, demonstrates that the slower band does indeed contain GFP. β2AR normally sequesters poorly in COS cells, and this has been correlated to the relatively poor expression of endogenous β-arrestins in COS cells. Menard et al., *Mol. Pharmacol.* 51:800 (1997); Zhang et al., *J. Biol. Chem.* 271:18302 (1996). Overexpression of exogenous β-arrestin enhances β2AR sequestration in these cells; similarly, as shown herein, βarr2-GFP overexpression in COS cells augmented β2AR internalization (FIG. 2B), demonstrating that βarr2-GFP is biologically active and equivalent to native β-arrestin.

Biochemical evidence indicates that β-arrestins are predominantly cytosolic proteins. Ferguson et al., *Can. J. Physiol. Pharmacol.* 74:1095 (1996). The present inventors, using confocal microscopy of βarr2-GFP in HEK-293 cells (FIG. 3A, left panel), confirmed that βarr2-GFP is distributed throughout the cytosol and excluded from the nucleus. The present data also establish for the first time that β-arrestin is not predominantly compartmentalized at the plasma membrane in the absence of agonist but that, upon addition of saturating concentrations of an agonist to the cell medium, β-arrestin is translocated from cell cytosol to cell membrane. Where β-arrestin is conjugated to an optically detectable molecule such as GFP, as shown herein, a rapid and readily observable optical enhancement of the membrane and a concomitant loss of cytosolic optical signals occurs (see FIGS. 3A and 3B, where membrane fluorescence is enhanced and cytosol fluorescence is decreased due to translocation of the β-arrestin-GFP chimera).

To investigate whether the intracellular translocation of β-arrestin targeted binding sites in the plasma membrane other than the β2AR, the present inventors first crosslinked the receptors using monoclonal antibodies. As reported herein and shown in FIG. 4, the geometry of the agonist-induced time dependent translocation of β-arrestin to the plasma membrane mimicked the distribution of pre-aggregated β2ARs, indicating that the targeted site of β-arrestin is indeed β2AR or an associated component.

It has been postulated that phosphorylation of GPCRs by GRKs facilitates desensitization by increasing their affinity for β-arrestins. Gurevich et al, *J. Biol. Chem.* 268:16879 (1993); Gurevich et al., *J. Biol. Chem.* 268:11628 (1993). When expressed in HEK-293 cells and exposed to agonist, mutant Y326A-β2ARs are not significantly phosphorylated by endogenous GRKs (Ferguson et al., *J. Biol. Chem.,* 270:24782 (1995). Therefore, the present inventors utilized this mutant receptor to investigate the above question of β-arrestin affinity in vivo. Y326A-β2AR was cotransfected with βarr2-GFP into HEK cells in the absence and presence of co-transfected GRK. If the above hypothesis were true, reversal of phosphorylation impairment by overexpressed GRKs would result in a noticeable difference in βarr2-GFP translocation. As reported herein, without added GRK, βarr2-GFP translocation in response to agonist proceeded poorly; with the addition of GRK, βarr2-GFP translocation to the plasma membrane was much more robust (FIG. 5), indicating the importance of phosphorylation to βarrestin activity.

The present inventors determined that translocation of βarrestin from the cell cytosol to the cell membrane is an indicator of agonist stimulation of GPCR activity, and that a chimeric protein comprising βarrestin and the detectable molecule GFP was capable of detectably displaying the real-time translocation of βarrestin in response to agonist activation of GPCRs.

The results presented herein establish that βarrestin targets GPCRs or an associated molecule following agonist binding and receptor phosphorylation. These data demonstrate a biological behavior for βarrestin that has only been postulated from biochemical studies, and characterize for the first time how βarrestin compartmentalization changes after initiation of receptor signal transduction. Agonist activation of a GPCR ultimately culminates in the association of βarrestins with GPCRs, thus the visualization of the agonist mediated βarrestin translocation process provides a universal indicator of GPCR activation.

The present inventors have demonstrated that GPCR signal transduction induces a rapid, substantial increase in the relative and absolute amount of plasma membrane bound βarrestin. The agonist-mediated redistribution of βarrestin coupled to a detectable molecule provides an optical amplification of the extracellular signals transduced by GPCRs, and this occurs simultaneously with, or within the same time frame as, the chemical amplification normally provided by second messenger cascades. Chimeras of βarrestin and a detectable molecule are useful for the study of βarrestin kinetics and GPCR related behavior such as endocytosis. Additionally, such chimeras are useful as biosensors for signaling when GPCRs become activated, and provide methods of screening compounds for GPCR activity, and screening orphan GPCRs for ligand responsiveness. In addition, the ability of co-transfected GRKs to enhance both the rate and extent of βarrestin translocation indicate that the present methods and constructs can also be used to monitor GRK activity, as well as monitor drugs, proteins and compounds for activation or inhibition of the GRK/βarrestin process.

The present invention provides a method for screening compounds for GPCR agonist activity, comprising: a) providing a cell expressing a known or unknown GPCR and containing a chimeric protein comprising a βarrestin protein and a visually detectable protein; b) exposing the cell to a test compound; and c) detecting translocation of the detectable molecule from the cytosol of the cell to the membrane edge of the cell; where translocation of the detectable molecule from the cytosol to the membrane edge of the cell indicates activation of the GPCR and, accordingly, the GPCR activating effect of the test compound. Translocation of the chimeric protein is evidenced by an increase in the intensity of detectable signal located at the membrane edge (and/or a decrease in the cytosol), where the change occurs after exposure to the test compound. Translocation may thus be detected by comparing changes in the detectable signal in the same cell over time (i.e., pre and post test compound exposure). Alternatively, a test cell may be compared to a control cell (no exposure to test compound), or a test cell may be compared to a pre-established standard. If a known agonist is available the present methods can be used to screen for and study GPCR antagonists. Additionally, the membrane association of βarrestin should be increased by expression of an excess of receptor or by a constitutively active GPCR that undergoes phosphorylation by GRKs even in the absence of agonist. Therefore, the present methods can be used to monitor for inverse agonists of GPCRs.

Methods of detecting the intracellular translocation of the chimeric protein will depend on the particular detectable protein utilized; one skilled in the art will be able to readily devise detection methods suitable for particular detectable molecules, given the teachings of the present specification and knowledge in the art. In a preferred embodiment, the visually detectable protein is a green-fluorescent protein (GFP) as discussed below.

The methods of the present invention provide easily detectable results. The translocation of βarrestin coupled to a detectable molecule such as GFP, in response to GPCR activation, results in a relative enhancement of the detectable signal at the cell edge (i.e., at the cell membrane). In addition, the concomitant decrease in detectable signal from the cell cytosol means that 'background noise' (detectable signals which do not change in response to GPCR activation) is minimized. In certain cells, activation of GPCRs will result in essential clearing of detectable signal from the cytosol, and a 100-fold increase (or more) in the detectable signal at the cell membrane. In the present methods, it is preferred that the detectable signal at the membrane edge increase, after GPCR activation, at least two-fold, more preferably at least 3-fold, and more preferably at least 5-fold or at least ten-fold.

As used herein, the introduction of a chimeric protein into a cell may be accomplished by introducing into the cell (or the cell's ancestor) a nucleic acid (e.g., DNA or RNA) sequence or construct encoding the chimeric protein, and culturing the cell in an environment which allows expression of the chimeric protein. Introduction of nucleic acids encoding the chimeric protein, or introduction of the protein itself, into a cell may be carried out by any of the many suitable methods which are known in the art, including transfection, electroporation, microinjection, and liposome delivery.

The present invention provides a DNA construct comprising a promoter, DNA encoding a βarrestin protein operatively associated therewith, and DNA encoding a visually detectable marker protein operatively associated therewith. The promoter is operatively associated with the encoding DNA; DNA encoding βarrestin may be 5' from DNA encoding the visually detectable marker, or vice versa. In a preferred embodiment, the DNA encoding a visually detectable marker encodes a green-fluorescent protein (GFP). Vectors comprising such DNA constructs are a further aspect of the present invention.

The present invention further provides conjugates (such as chimeric proteins or fusion proteins) which comprise a βarrestin protein and a visually detectable protein. In a preferred embodiment, the visually detectable protein is a green-fluorescent protein (GFP).

The present invention further provides a cell comprising a DNA molecule, which DNA molecule comprises, in the 5' to 3' direction, a promoter, DNA encoding a βarrestin protein operatively associated therewith, and DNA encoding a visually detectable marker protein operatively associated therewith. In a preferred embodiment, the DNA encoding a visually detectable marker encodes a green-fluorescent protein (GFP).

The cells of the present invention may be used to detect the presence of specific molecules in various kinds of samples such as, e.g., aqueous samples, biological samples (for example blood, urine or saliva), environmental samples, or industrial samples. In such uses, the cells contain a GPCR whose agonists are known. Activation of the GPCR and the concomitant translocation of the detectable signal from the cytosol to the membrane edge indicates the presence of the agonist for the GPCR. A cell used in such a method may contain only a single type of known GPCR, or a variety of known GPCRs. Such detection will be useful for medical and veterinary diagnostic purposes; industrial purposes; and screening for drugs or chemicals of abuse or biological toxins that affect GPCR-mediated signal transduction.

The cells of the present invention may be deposited on, affixed to, supported by, or immobilized on a substrate. The substrate may be of any suitable material which is not harmful or detrimental to the living cells deposited thereon, i.e., which is bio-compatible with the living material deposited thereon. The substrate may be rigid, semi-rigid or flexible; and may be opaque, transparent, or semi-transparent. The size, geometry and other physical characteristics of the substrate will be dictated by the intended use, as will be apparent to one skilled in the art. Suitable substrates include, but are not limited to, plastics, glass, ceramics, silica, biocompatible monomer and polymer compositions, semiconductor materials, fiber optic materials, polystyrene, membranes, sephadex, and bio-organic materials. Examples of biocompatible materials are provided in U.S. Pat. Nos. 5,578,079; 5,575,997 and 5,582,834 to Leung and Clark; and U.S. Pat. No. 5,522,896 to Prescott.

The present invention further provides methods for screening for the presence of a GPCR agonist in a solution which comprises: a) providing a cell expressing a known or unknown GPCR and containing a chimeric protein comprising a βarrestin protein and a visually detectable protein; b) exposing the cell to a test solution; and c) detecting translocation of the detectable molecule from the cytosol of the cell to the membrane edge of the cell; where translocation of the detectable molecule from the cytosol to the membrane edge of the cell indicates activation of the GPCR and, accordingly, the GPCR agonist effect of the test solution. Translocation of the chimeric protein is evidenced as discussed above.

The present invention further provides methods for screening for the presence of a GPCR antagonist in a solution which comprises: a) providing a cell expressing a GPCR and containing a chimeric protein comprising a βarrestin protein and a visually detectable protein; b) exposing the cell to a test compound; then c) exposing the cell to a known agonist to the GPCR expressed in the cell; and d) detecting translocation of the detectable molecule from the cytosol of the cell to the membrane edge of the cell. If the test compound contains an antagonist, translocation of the detectable molecule will be delayed for a period of time corresponding to duration of antagonist action on the receptor (which time period will vary depending on the antagonist and/or the receptor). Translocation of the detectable molecule from the cytosol to the membrane edge of the cell indicates activation of the GPCR by the agonist. Accordingly, when translocation does not occur or is delayed (compared to that which would occur in the absence of test compound), the test compound contains an antagonist to the GPCR. Absence or delay of translocation may be assessed by comparison to a control cell (not exposed to test compound) or to a predetermined standard. Translocation of the chimeric protein is evidenced as discussed above. Exposure to the test compound and the known agonist may occur at essentially the same time, or exposure to the agonist may occur subsequent to exposure to the test compound. As used herein, subsequent exposure refers to exposure within the time period during which a potential antagonist would be expected to be interacting with the GPCR (i.e., binding to or bound to the GPCR).

The present invention further provides methods for screening a cell for the presence of a GPCR, comprising: a) providing a test cell; b) introducing into the test cell a chimeric protein comprising a βarrestin protein and a visually detectable protein; and then c) exposing the cell to a test solution containing a known agonist to a GPCR; and d) detecting translocation of the detectable molecule from the cytosol of the cell to the membrane edge of the cell; where translocation of the detectable molecule from the cytosol to the membrane edge of the cell indicates activation of a GPCR and, accordingly, that the test cell contains such a GPCR. Translocation of the chimeric protein is evidenced as discussed above.

The present invention further provides methods for screening a cell population for the presence of cells containing GPCRs, comprising: a) providing a population of test cells, said test cells containing chimeric proteins comprising a βarrestin protein and a visually detectable protein; and then b) exposing the cell population to a test solution containing an agonist to a GPCR; and d) detecting those cells in which translocation of the detectable molecule from the cytosol of the cell to the membrane edge of the cell occurs; where translocation of the detectable molecule from the cytosol to the membrane edge of a cell indicates activation of a GPCR and, accordingly, that the cell in question contains a GPCR. Translocation of the chimeric protein is evidenced as discussed above. Populations of cells to be screened include a collection of individual cells, a tissue comprising a plurality of similar cells, an organ comprising a plurality of related cells, or an organism comprising a plurality of tissues and organs.

As used herein, 'exposing' a cell to a test compound or solution means bringing the cell exterior in contact with the test compound or solution. Where the test compound or solution is being screened for GPCR ligand activity, exposure is carried out under conditions that would permit binding of a GPCR ligand to a receptor expressed in that cell. As used herein, 'translocation' of βarrestin refers to movement of the βarrestin molecule from one area of the cell to another.

The present methods may further be used to assess or study the effects of any molecule in the GPCR pathway which exerts its effect upstream of βarrestin binding (i.e., prior to βarrestin binding to the phosphorylated GPCR). Thus the present invention provides methods for assessing GPCR pathway functions in general. As used herein, the GPCR pathway refers to the series of events which starts with agonist activation of a GPCR followed by desensitization of the receptor via G protein-coupled receptor kinase (GRK) phosphorylation and βarrestin binding.

In a broad sense the present invention thus provides a method of screening test compounds and test conditions for the ability to affect (activate or inhibit, enhance or depress) a GPCR pathway, and provides methods of assessing GPCR pathway function in a cell in general. In the present methods, the extent of translocation of βarrestin is indicated by the degree of detectable changes in the cell; the extent of βarrestin translocation is an indicator of the extent of GPCR pathway completion. The relative extent of translocation under varied test conditions may be compared, or a test condition may be compared to a control condition or to a predetermined standard.

For example, the specificity and effects of various kinases (including those known to interact with GPCR pathways and those not previously known to interact with GPCRs) for a specific GPCR or a group of GPCRs may be assessed by providing a test kinase to a test cell expressing a GPCR and containing a detectable βarrestin molecule, exposing the cell to a GPCR agonist, and assessing the translocation of detectable βarrestin from the cell cytosol to the cell membrane (see Example 7 herein). Translocation of the βarrestin to the cell membrane indicates that the test kinase, in response to agonist occupancy of the receptor, is able to bind to and phosphorylate the receptor, so that βarrestin will then bind to the kinase phosphorylated receptor and prevent subsequent interaction with the appropriate G-protein. In similar ways, the function of altered, recombinant or mutant kinases may be assessed; compounds may be screened for the ability to activate or inhibit the GPCR pathway, G protein-coupled receptor kinases, or βarrestin binding; and the function of G-proteins may be assessed. For example, the following test conditions may be assessed using methods as described herein: the effects of G-proteins (including natural, heterologous, or artificially altered G-proteins) within the test cell; exposure of the test cell to known or putative GPCR ligands; and co-expression of a second receptor in the test cell expressing a GPCR.

Still further, the present methods allow the screening of βarrestins (naturally occurring, artificially introduced, or altered, mutant or recombinant) for the ability to bind to a phosphorylated GPCR. In such methods, the test βarrestin is conjugated to a detectable molecule such as GFP, and is placed within a cell containing a GPCR. The cell is exposed to a known agonist of the GPCR, and translocation of the detectable molecule from the cytosol of the cell to the membrane edge of the cell is detected. The translocation of the detectable molecule indicates that the test βarrestin protein is able to bind to the phosphorylated GPCR. As in other methods of the present invention, the translocation may be compared to a control cell containing a known βarrestin, or to a predetermined standard.

G Protein Coupled Receptors

GPCRs suitable for use in the present methods are those in which agonist binding induces G protein-coupled receptor kinase (GRK) phosphorylation; translocation of arrestin from the cytosol of the cell to the cell membrane subsequently occurs. As it is believed that virtually all members of the GPCR superfamily desensitize via this common mechanism, examples of suitable types of GPCRs include but are not limited to beta and alpha adrenergic receptors; GPCRs binding neurotransmitters (such as dopamine); GPCRs binding hormones; the class of odorant receptors (taste, smell and chemotactic receptors as found in nasal mucosa and the tongue, and on sperm, egg, immune system cells and blood cells); the class of type II GPCRs including secretin, glucagon, and other digestive tract receptors; light-activated GPCRs (such as rhodopsin); and members of the type III family of GPCRs which include but are not limited to metabotopic glutamate receptors and GABA.sub.B receptors. In addition to naturally occurring GPCRs, GPCRs may be specifically engineered or created by random mutagenesis. Such non-naturally occurring GPCRs may also be utilized in and screened by the present methods. The present methods may be utilized with any membrane receptor protein in which agonist binding results in the translocation of βarrestin. Such receptors include growth factors that signal through G proteins.

Automated Screening Methods

The methods of the present invention may be automated to provide convenient, real time, high volume methods of screening compounds for GPCR ligand activity, or screening for the presence of a GPCR ligand in a test sample. Automated methods are designed to detect the change in concentration of labelled βarrestin at the cell membrane and/or in the cytosol after exposure to GPCR agonist. The alteration of βarrestin distribution can be detected over time (i.e., comparing the same cell before and after exposure to a test sample), or by comparison to a control cell which is not exposed to the test sample, or by comparison to pre-established indicia. Both qualitative assessments (positive/negative) and quantitative assessments (comparative degree of translocation) may be provided by the present automated methods, as will be apparent to those skilled in the art.

It is thus a further object of the present invention to provide methods and apparatus for automated screening of GPCR activity, by detecting the translocation of detectably labeled βarrestin from cell cytosol to cell membrane in response to agonist activation of GPCRs. The translocation may be indicated by an alteration in the distribution of a detectable signal within a cell over time, between a test cell and a control cell, or by comparison to previously established parameters. In particular, according to one embodiment of the present invention, a plurality of cells expressing GPCRs and containing chimeric proteins comprising a detectable molecule and a βarrestin molecule are provided. Indicia of the distribution of the detectable molecules are then measured using conventional techniques. In various embodiments, (a) measurement of optical indicia occurs before and after the addition of a test sample to a cell, and the time point measurements are compared; (b) optical indicia are measured in a test cell exposed to a test sample and in a non-exposed control cell, and these measurements are compared; and (c) measurement of a test cell after addition of a test sample is compared to preestablished parameters. The optical indicia being measured may be fluorescence signals (e.g., fluorescence intensities) if the detectable molecule of the chimeric βarrestin protein is a fluorescent indicator such as GFP. Other optical indicia that are suitable for real-time measurement may also be used, as will be apparent to those skilled in the art.

An embodiment of the present invention includes an apparatus for determining GPCR response to a test sample. This apparatus comprises means, such as a fluorescence measurement tool, for measuring indicia of the intracellular distribution of detectable βarrestin proteins in at least one test cell, and optionally also in a control or calibration cell. Measurement points may be over time, or among test and control cells. A computer program product controls operation of the measuring means and performs numerical operations relating to the above-described steps. The preferred computer program product comprises a computer readable storage medium having computer-readable program code means embodied in the medium. Hardware suitable for use in such automated apparatus will be apparent to those of skill in the art, and may include computer controllers, automated sample handlers, fluoresence measurement tools, printers and optical displays. The measurement tool may contain one or more photodetectors for measuring the fluorescence signals from samples where fluorescently detectable molecules are utilized in the detectable βarrestin construct. The measurement tool may also contain a computer-controlled stepper motor so that each control and/or test sample can be arranged as an array of samples and automatically and repeatedly positioned opposite a photodetector during the step of measuring fluorescence intensity.

The measurement tool is preferably operatively coupled to a general purpose or application specific computer controller. The controller preferably comprises a computer program product for controlling operation of the measurement tool and performing numerical operations relating to the above-described steps. The controller may accept set-up and other related data via a file, disk input or data bus. A display and printer may also be provided to visually display the operations performed by the controller. It will be understood by those having skill in the art that the functions performed by the controller may be realized in whole or in part as software modules running on a general purpose computer system. Alternatively, a dedicated stand-alone system with application specific integrated circuits for performing the above described functions and operations may be provided.

As provided above, the indicia of βarrestin distribution may take the form of fluorescent signals, although those skilled in the art will appreciate that other indicia are known and may be used in the practice of the present invention, such as may be provided by labels that produce signals detectable by fluorescence, radioactivity, colorimetry, X-ray diffraction or absorption or magnetism. Such labels include, for example, fluorophores, chromophores, radioactive isotopes (e.g., $^{32}P$ or $^{125}I$) and electron-dense reagents.

The expression or transcription cassette may be provided in a DNA construct which also has at least one replication system. For convenience, it is common to have a replication system functional in *Escherichia coli*, such as Co1E1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host. The markers may be protection against a biocide, such as antibiotics, toxins, heavy metals, or the like; may provide complementation, by imparting prototrophy to an auxotrophic host; or may provide a visible phenotype through the production of a novel compound in the plant.

The various fragments comprising the various constructs, expression cassettes, markers, and the like may be introduced consecutively by restriction enzyme cleavage of an appropriate replication system, and insertion of the particular construct or fragment into the available site. After ligation and cloning the DNA construct may be isolated for further manipulation. All of these techniques are amply exemplified in the literature as exemplified by J. Sambrook et al., *Molecular Cloning. A Laboratory Manual* (2d Ed. 1989)(Cold Spring Harbor Laboratory).

Arrestin Knockout Mice

The production of βarrestin knockout mice can be carried out in view of the disclosure provided herein and in light of techniques known to those skilled in the art, such as described in U.S. Pat. Nos. 5,767,337 to Roses et al.; 5,569,827 to Kessous-Elbaz et al.; and 5,569,824 to Donehower et al. (the disclosures of which applicants specifically intend to be incorporated by reference herein in their entirety); and A. Harada et al., *Nature* 369, 488 (1994). Particularly preferred mice for carrying out the present invention are also disclosed below.

1. Assay techniques. The step of determining whether or not βarrestin binding to the phosphorylated μ opioid receptor is inhibited by the test compound may be carried out by any suitable technique, including in vitro assay and in vivo assay (e.g., in a cell that contains the βarrestin and the phosphorylated μ opioid receptor). A particularly suitable technique for in vivo assay is as described previously. In general, this technique involves providing a cell that expresses μ opioid receptor as a G-protein coupled receptor, and contains the βarrestin protein conjugated to an optically detectable molecule (e.g., green fluorescent protein). The test compound is then introduced into the cell (e.g., by microinjection, by electroporation, by suspending the cell in an aqueous solution that contains the test compound, by contacting the cell to liposomes that contain the test compound, by insertion of a heterologous nucleic acid into the cell that encodes and expresses the test compound, etc.). Translocation of the molecule from the cytosol of the cell to the membrane edge of the cell is then monitored or examined, with the inhibition of such translocation indicating that the test compound inhibits the binding of βarrestin to the phosphorylated μ opioid receptor. If desired, phosphorylation of the μ opioid receptor can be induced or enhanced by any suitable means, such as contacting a μ opioid receptor agonist such as morphine to the cell in an amount effective to induce phosphorylation (e.g., by adding the agonist to the culture medium or liquid medium in which the cell is contained). The cell is preferably a mammalian cell, but any suitable cell can be employed, including bacterial cells, yeast cells, fungal cells, plant cells, and other animal cells, so long as they express μ opioid receptor and phosphorylate, or can be induced to phosphorylate, the same, and contain the desired βarrestin protein coupled to an optically detectable molecule (e.g, either by exogenous introduction or expression of the βarrestin conjugate therein). Any suitable βarrestin may be employed as described above, with βarrestin-2 being preferred.

2. Test compounds. The present invention can be used with test compounds (or "probe molecules"), or libraries (where groups of different probe molecules are employed), of any type. In general, such probe molecules are organic compounds, including but not limited to oligomers, non-oligomers, or combinations thereof. Nonoligomers include a wide variety of organic molecules, such as heterocyclics, aromatics, alicyclics, aliphatics and combinations thereof, comprising steroids, antibiotics, enzyme inhibitors, ligands, hormones, drugs, alkaloids, opioids, benzodiazepenes, terpenes, porphyrins, toxins, catalysts, as well as combinations thereof. Oligomers include peptides (that is, oligopeptides) and proteins, oligonucleotides (the term oligonucleotide also referred to simply as "nucleotide", herein) such as DNA and RNA, oligosaccharides, polylipids, polyesters, polyamides, polyurethanes, polyureas, polyethers, poly (phosphorus derivatives) such as phosphates, phosphonates, phosphoramides, phosphonamides, phosphites, phosphinamides, etc., poly (sulfur derivatives) such as sulfones, sulfonates, sulfites, sulfonamides, sulfenamides, etc., where for the phosphorous and sulfur derivatives the indicated heteroatom for the most part will be bonded to C, H, N, O or S, and combinations thereof. Numerous methods of synthesizing or applying such probe molecules on solid supports (where the probe molecule may be either covalently or non-covalently bound to the solid support) are known, and such probe molecules can be made in accordance with procedures known to those skilled in the art. See, e.g., U.S. Pat. No. 5,565,324 to Still et al., U.S. Pat. No. 5,284,514 to Ellman et al., U.S. Pat. No. 5,445,934 to Fodor et al. (the disclosures of all United States patents cited herein are to be incorporated herein by reference in their entirety).

3. Pain control and active compounds. As noted above, the present invention provides a method of controlling pain in a subject, comprising inhibiting βarrestin binding to the phosphorylated μ opioid receptor in said subject in an amount effective to induce or enhance analgesia in the subject. The method may be carried out with or without concurrently administering a μ opioid receptor agonist such as morphine (or other opiate, as described below). When carried out without concurrent administration of μ opioid receptor, the analgesic activity relies upon the activity of endogenous opioid receptor agonists.

The inhibiting of βarrestin binding (preferably βarrestin-2 binding) to phosphorylated μ opioid receptor can be carried out directly or indirectly by any suitable means, including but not limited to knockout of the βarrestin gene as described herein, disabling or downregulating the kinase responsible for phosphorylation of the μ opioid receptor, administration of an antisense oligonucleotide that downregulates expression of the βarrestin, or the administration of an active compound that competitively inhibits binding of the βarrestin to phosphorylated μ opioid receptor (which may be identified by the assay techniques described above). Obviously, functional μ opioid receptor itself must remain in the cells (particularly nerve cells) of the subject so that the primary analgesic activity of the μ opioid receptor agonist can be exerted.

Compounds produced or identified as active compounds by application of the assay procedures described herein to the test compounds or probe molecules described herein are useful in vitro and in vivo as μ opioid receptor agonists (in that they enhance the activity of opioids, although they do not bind to the same site as an opioid), are useful in enhancing the efficacy, potency, or analgesic activity of μ opioid receptor agonists. Such compounds are also useful in vivo in controlling pain in a subject in need thereof. By "controlling pain", "control of pain" and the like herein is meant partially or completely inhibiting a pain response or perception of pain in a subject, and/or partially or fully inducing local or general analgesia in a subject, either alone or in combination with another active agent administered to the subject such as a μ opioid receptor agonist (e.g., morphine). Subjects that may be treated by the compounds identified by the present invention include both human subjects and animal subjects (e.g., dogs, cats, horses, cattle) for veterinary purposes.

Thus, as noted above, further aspects of the present invention include active compounds produced or identified by the methods described hereinabove and pharmaceutical formulations of the same (e.g., said compound in a sterile pyrogen-free saline solution), along with the use of such compounds for the preparation of a medicament for the potentiation of the activity of μ opioid receptor agonists such as morphine, and/or for the control of pain, in a subject in need thereof, either alone or in combination with a μ opioid receptor agonist such as morphine.

In addition to morphine, other μ opioid receptor agonists, typically opiates, that may be used in conjunction with the present invention include, but are not limited to, codeine, oxycodeine, hydromorphone, diamorphine, methadone, fentanyl, sufentanil, buprenorphine, meperidine (Demerol®), etc.

The active compounds described above may be combined with a pharmaceutical carrier in accordance with known techniques to provide a pharmaceutical formulation useful carrying out the methods described above. See, e.g., Remington, *The Science And Practice of Pharmacy* (9h Ed, 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous), topical (i.e., both skin and mucosal surfaces), the most suitable route in any given case will depend on the nature and severity of the condition being treated and on the nature of the particular active compound which is being used.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of the present invention+, or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3(6):318 (1986)) and typically take the form of an optionally buffered aqueous solution of the active compound. Suitable formulations comprise citrate or bis\tris buffer (pH 6) or ethanol/water and contain from 0.1 to 0.2 M active ingredient.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

The present invention is explained in greater detail in the following nonlimiting Examples. The examples which follow are set forth to illustrate the present invention, and are not to be construed as limiting thereof. As used herein, βarr2-GFP=βarrestin2 green fluorescent protein; GFP=green fluorescent protein; GPCR=G protein-coupled receptor; βARK=beta adrenergic receptor kinase; GRK=G protein-coupled receptor kinase; β2AR=β2 adrenergic receptor; HEK-293=human embryonic kidney cells; DMEM=Dulbecco's modified Eagle medium; and MEM=Minimal Essential Medium.

EXAMPLE 1

Materials and Methods

Materials: Isoproterenol was obtained from Sigma RBI. Anti-mouse antibody was obtained from Sigma Chemicals or Molecular Probes. Mouse monoclonal antibody against the 12CA5 epitope was obtained from Boehringer Mannheim. Cell culture media was obtained from Mediatech and fetal bovine serum from Atlanta Biologicals. Physiological buffers were from Gibco-Life Technologies Inc. Restriction enzymes were obtained from Promega or New England Biolabs, T4 ligase was from Promega, and Hot Tub DNA polymerase from Amersham. Commercially available plasmids containing variants of Green Fluorescent Protein were obtained from Clontech.

Cell Culture and Transfection: HEK-293 and COS cells were maintained and transfected as described by Barak et al., *Mol. Pharm.* 51:177 (1997). Cells containing both β2 adrenergic receptor and βarrestin constructs were transfected with between 5-10 µg of receptor cDNA in pcDNA1/AMP and 0.5-1 µg of βarr2-GFP cDNA per 100 mm dish. GRKs were expressed using 5 µg of transfected cDNA in pcDNA1/AMP per dish.

Confocal Microscopy: HEK-293 cells transfected as described above were plated onto 35 mm dishes containing a centered, 1 cm well formed from a hole in the plastic sealed by a glass coverslip. Primary and secondary antibody labeling of live cells were performed at 37° C. for 30 minutes in media without serum in a 5% $CO_2$ incubator. Cells were washed three times between applications. Cells plated as above in MEM or DMEM buffered with 20 mM Hepes were viewed on a Zeiss laser scanning confocal microscope.

Sequestration: Flow cytometry analysis was performed using techniques known in the art, as described in Barak et al., *J. Biol. Chem.* 269:2790 (1994).

EXAMPLE 2

Construction of βarrestin2-GFP Plasmid

βarrestin2 cDNA in the plasmid pCMV5 was used as a template. Oligonucleotide primers surrounding a distal XhoI restriction site and the C-terminal stop codon of βarrestin2 were used to replace the stop codon with an in frame BamHI restriction site by directed mutagenesis (Valette et al. *Nucleic Acids Res.* 17:723 (1989); Attramadal et al., *J. Biol. Chem.* 267:17882 (1992); Lohse et al., *Science* 248:1547 (1990)). The XhoI, BamHI segment was isolated. This segment was ligated to the N-terminal portion of βarrestin cDNA (cut from pCMV5 by SacI and XhoI) in the polylinker of a plasmid that had been previously digested with SacI and BamHI and that contained S65T-Green Fluorescent Protein distal and in frame to the site of βarrestin cDNA insertion. Lohse et al., *Science* 248:1547 (1990). The resulting βarrestin-GFP construct was isolated following insertion and growth in *E. coli*. Constructs were verified by sequencing.

Figure 2A:
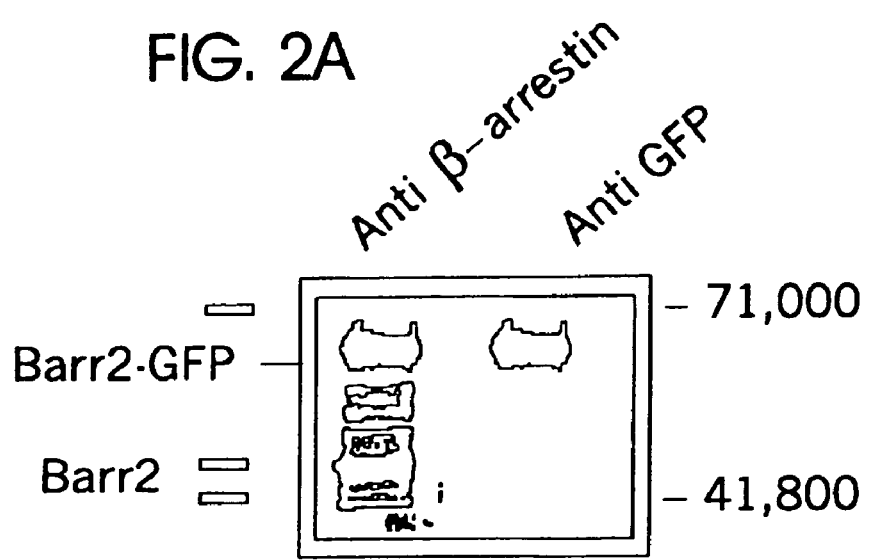
FIG. 2A provides the results of a Western Blot of homogenates of HEK-293 cells expressing the βarr2-GFP conjugate as well as endogenous β-arrestin2. βarr2 indicates endogenous cellular β-arrestin2; βarr2-GFP indicates βarrestin2-GFP conjugate; approximate molecular weights are indicated to the right of the gel. Lane 1 was treated with anti-βarrestin antibody; Lane 2 with anti-GFP antibody.

A linear model of the βarrestin2/S65T-GFP conjugate is provided in FIG. 1.

EXAMPLE 3

Characterization of βarr2-GFP Expressed by HEK-293 Cells

Homogenates of HEK-293 cells transformed with the plasmid of Example 2 were studied using known Western Blot techniques. The results showed that HEK-293 cells expressed both endogenous βarrestin and the βarr2-GFP conjugate.

Western Blots of homogenates of HEK-293 cells transfected with the plasmid of Example 2 and expressing βarr2-GFP were performed. An equal amount of homogenate material was loaded into each of two lanes (FIG. 2A). The left lane was exposed to anti-βarrestin antibody (Menard et al., *Mol. Pharm.* 51:800 (1997)), whereas the right lane was exposed to a mouse monoclonal antibody against GFP. The βarr2-GFP fusion protein is approximately 50% larger than βarrestin2, and would thus be expected to migrate more slowly than βarrestin on SDS-Page.

Exposure to anti-βarrestin antibody revealed multiple bars (left lane); exposure to anti-GFP monoclonal antibody revealed a single bar (right lane). The position of endogenous cellular βarrestin2 is indicated by the intermediate bar in the left lane (βarr2). The heavy band just below 71,000 on the left lane (βarr2-GFP) is mirrored by a similar band in the right lane. In contrast, no band corresponding to endogenous cellular βarrestin 2 is observed with anti-GFP antibody exposure. The treatment of the right lane with anti-GFP antibody demonstrated that the slower band labeled by anti-βarrestin antibody contained GFP.

EXAMPLE 4

Biological Activity of βarrestin-GFP Conjugate

βarrestin activity can indirectly be assessed by measuring its effect on receptor sequestration (see Menard et al., *Mol. Pharm.* 51:800 (1997); Ferguson et al., *Science* 271:363 (1996)). The β2AR normally sequesters poorly in COS cells, and this has been correlated to the relatively poor expression of endogenous βarrestins (see Menard et al. *Mol. Pharmacol.* 51:800 (1997); Ferguson et al, *Science* 271:363 (1996)). Overexpression of exogenous βarrestins enhances β2AR sequestration in these cells. To demonstrate that the βarr2-GFP conjugate is a biologically active βarrestin, COS cells overexpressing βarr2-GFP were examined for augmentation of β2AR internalization, compared to the augmentation of βAR2 seen with the overexpression of βarrestin2. Results are shown in FIG. 2B.

Using epitope tagged βAR2 receptors, sequestration of βAR2 was studied in COS cells overexpressing either (1) exogenous βarrestin2 or (2) the βarr2-GFP conjugate. FIG. 2B shows the sequestration of β2AR in COS cells with and without overexpressed βarrestin2 (left two bars) and with and without overexpressed βarr2-GFP (right two bars). Agonist mediated β2AR sequestration increased from 15.+−0.7% to 39.+−0.5% in the presence of overexpressed βarrestin2; overexpression of βarr2-GFP similarly increased agonist mediated β2AR sequestration from 25.+−0.4% to 58.+−0.1%. Wild type βarrestin2 and βarr2-GFP enhanced β2AR sequestration equally well above control levels, producing a 2.5 and 2.4 fold increase in β2AR sequestration, respectively.

The above results indicated that the βarr2-GFP conjugate acts as a biologically active arrestin.

EXAMPLE 5

Agonist Mediated Translocation of βarr2-GFP

Agonist mediated translocation of the βarr2-GFP chimera from cell cytosol to membrane was studied using HEK-293 and COS cells transfected with plasmids containing cDNA for the β2AR receptor and for the βarr2-GFP conjugate.

HEK-293 and COS cells were transfected with plasmids containing 10 μg of cDNA for β2AR and 0.5-1.0 μg for βarr2-GFP. Cells were assessed using confocal microscopy to detect the inherent intracellular fluorescence of GFP.

Figure 3A:
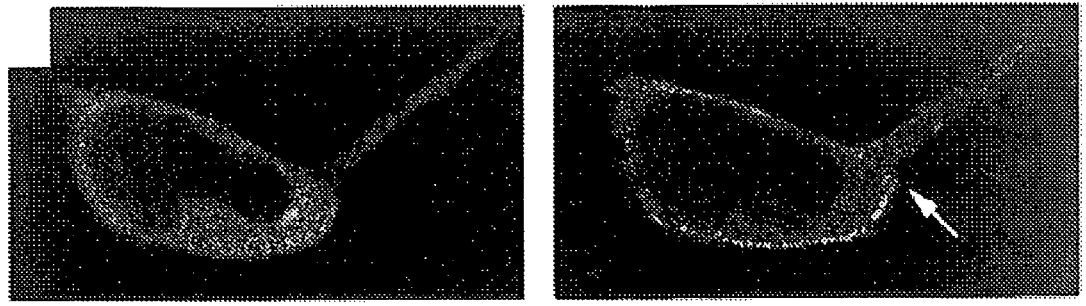
FIG. 3A: Confocal microscopy photomicrographs show βarr2-GFP translocation from cytosol (panel 1 at left) to membrane (panel 2 at right) in HEK-293 cells containing the β2AR, due to the addition of the βAR2 agonist isoproterenol. Bar=10 microns.

Transfected HEK-293 cells are shown in FIG. 3A, where panel 1 depicts cells prior to the addition of βAR2 agonist, and panel 2 depicts cells following the addition of agonist. Transfected COS cells are shown in FIG. 3B, where panel 1 depicts cells just prior to the addition of βAR2 agonist, and panel 2 depicts cells ten minutes after the addition of agonist.

As shown in FIG. 3A, βarr2-GFP distribution in HEK-293 cells was initially cytosolic (panel 1). No significant nuclear or membrane enhancement was apparent. Following the addition of the βAR2 agonist isoproterenol to the cell medium, the real-time agonist-mediated redistribution of βarr2-GFP was viewed using confocal microscopy. Ten minutes after isoproterenol addition (saturating concentrations), enhancement of membrane fluorescence was seen with a concomitant loss of cytosolic fluorescence, indicating that the βarr2-GFP distribution had shifted to the membrane (panel 2). These results establish that in HEK-293 cells containing the β2AR, βarr2-GFP expressed by the cell is translocated from cytosol to membrane following the addition of a βAR2 agonist. Exposure of the test cells to GPCR agonist enhanced membrane bound fluorescence ten-fold over that seen prior to agonist exposure.

Figure 3B:
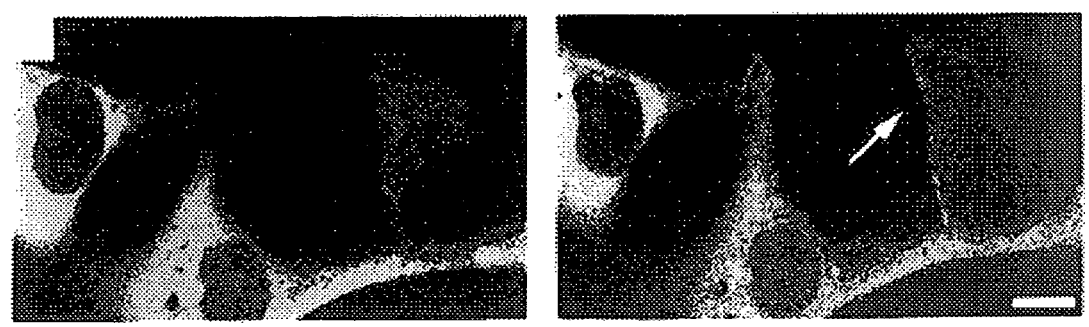
FIG. 3B: Confocal microscopy photomicrographs show βarr2-GFP translocation from cytosol (panel 1 at left) to membrane (panel 2 at right) in COS cells containing the β2AR, and due to addition of the βAR2 agonist isoproterenol. Bar=10 microns.

As shown in FIG. 3B, βarr2-GFP distribution in COS cells was initially cytosolic (panel 1). No significant nuclear or membrane enhancement was apparent. Following the addition of the βAR2 agonist isoproterenol to the cell medium, the real-time agonist-mediated redistribution of βarr2-GFP was viewed using confocal microscopy. Ten minutes after isoproterenol addition (saturating concentrations), enhancement of membrane fluorescence was seen with a concomitant loss of cytosolic fluorescence, indicating that the βarr2-GFP distribution had shifted to the membrane (panel 2). These results establish that in COS cells containing the β2AR, βarr2-GFP expressed by the cell is translocated from cytosol to membrane following the addition of a βAR2 agonist.

Comparing FIGS. 3A and 3B shows that the fluorescent signal is reduced in COS cells as compared to HEK cells, reflecting the lower efficiency of sequestration of the β2AR in COS cells. However, even in COS cells the shift of βarr2-GFP in COS cells from cytosol to membrane following the addition of βAR2 agonist is clearly discernible due to the fluorescence of the GFP moiety.

Figure 6A:
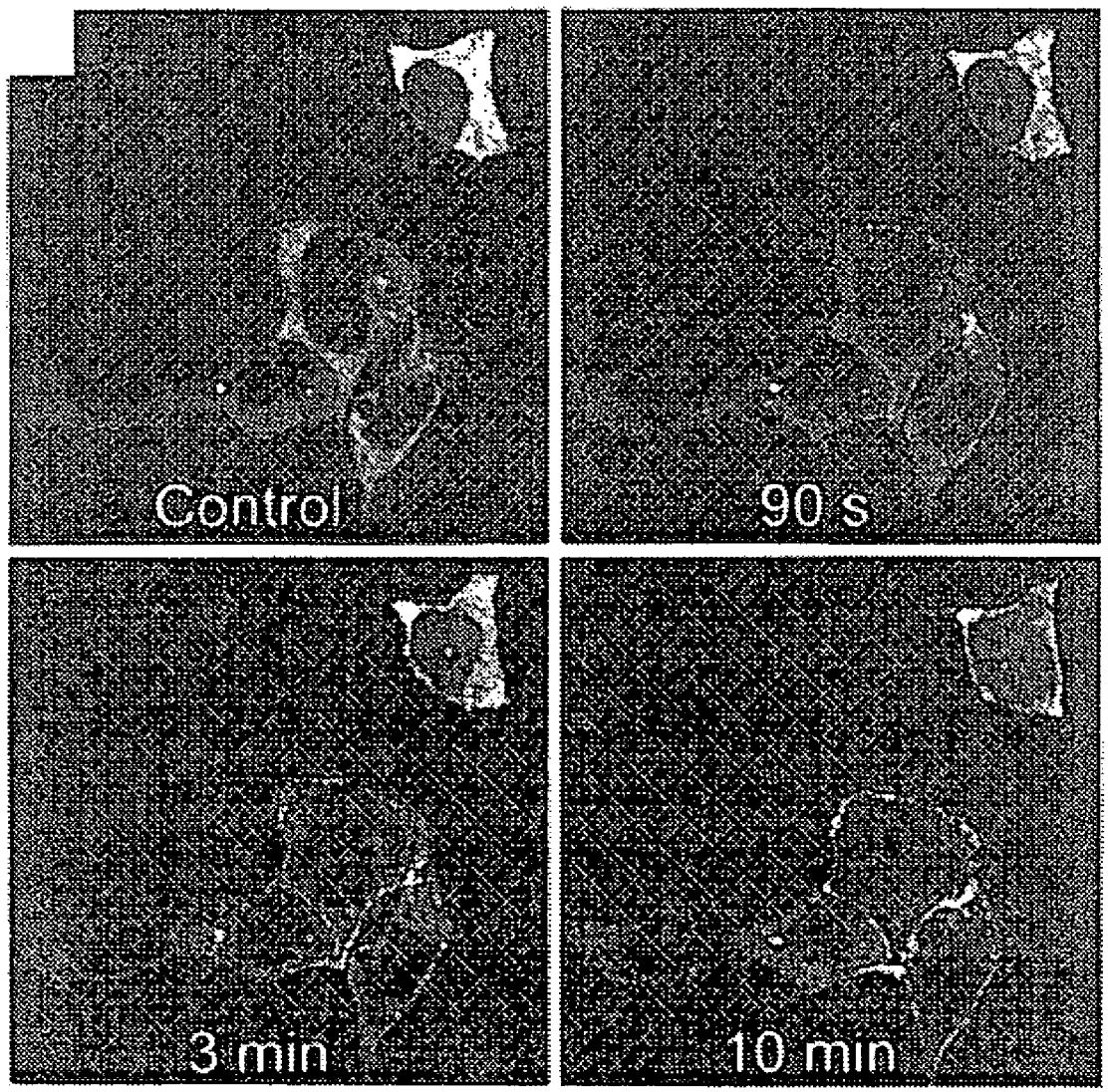
FIG. 6A depicts the agonist-induced time dependent translocation of βarr2-GFP to beta2 adrenergic receptors in a representational HEK-293 cell.
Figure 6B:
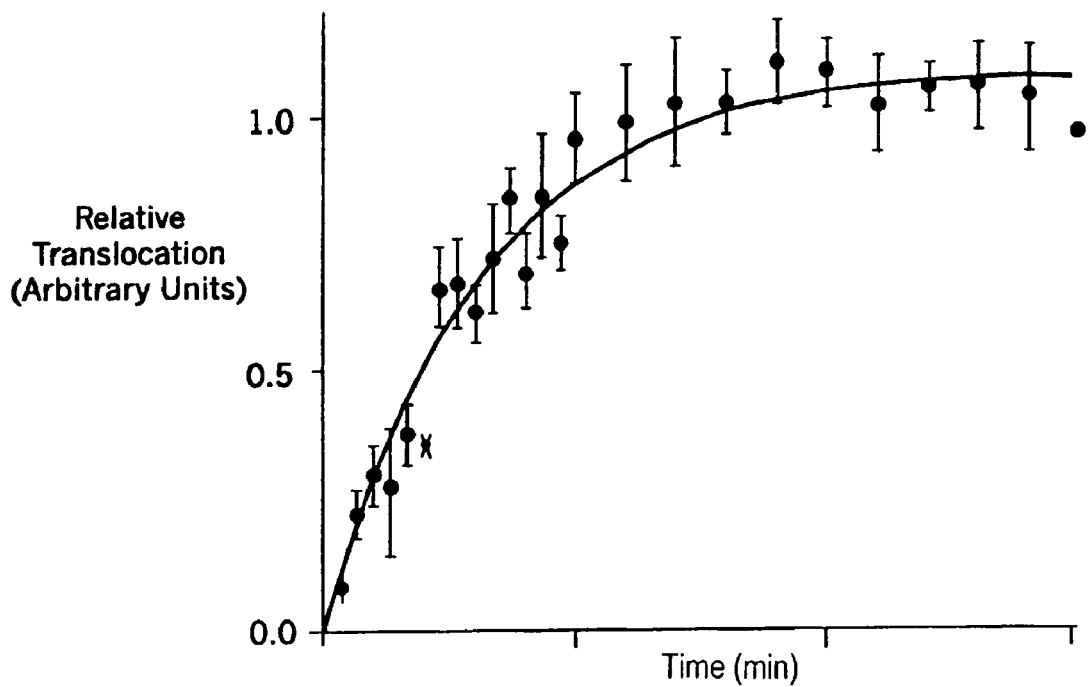
FIG. 6B graphs the time course of agonist-induced translocation of βarr2-GFP to beta2 adrenergic receptors in HEK-293 cells; this graph is quantitative and is based on the responses of a plurality of cells.
Figure 6D:
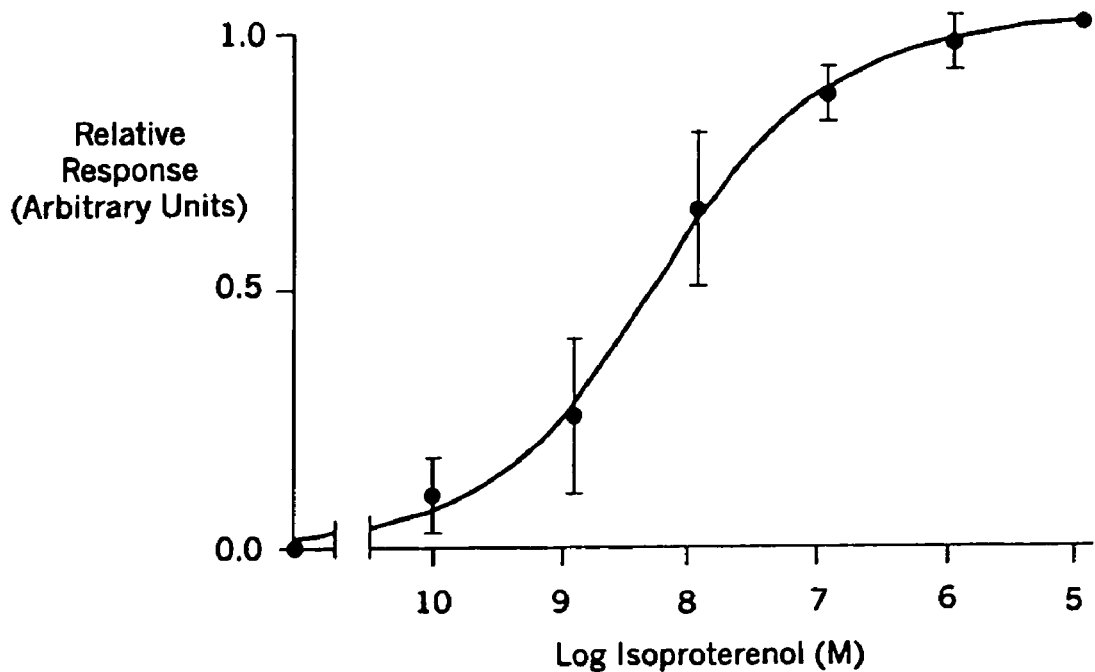
FIG. 6D graphs the dose dependent agonist-induced translocation of βarr2-GFP to beta2 adrenergic receptors in HEK-293 cells; this graph is quantitative and is based on the responses of a plurality of cells.
Figure 6C:
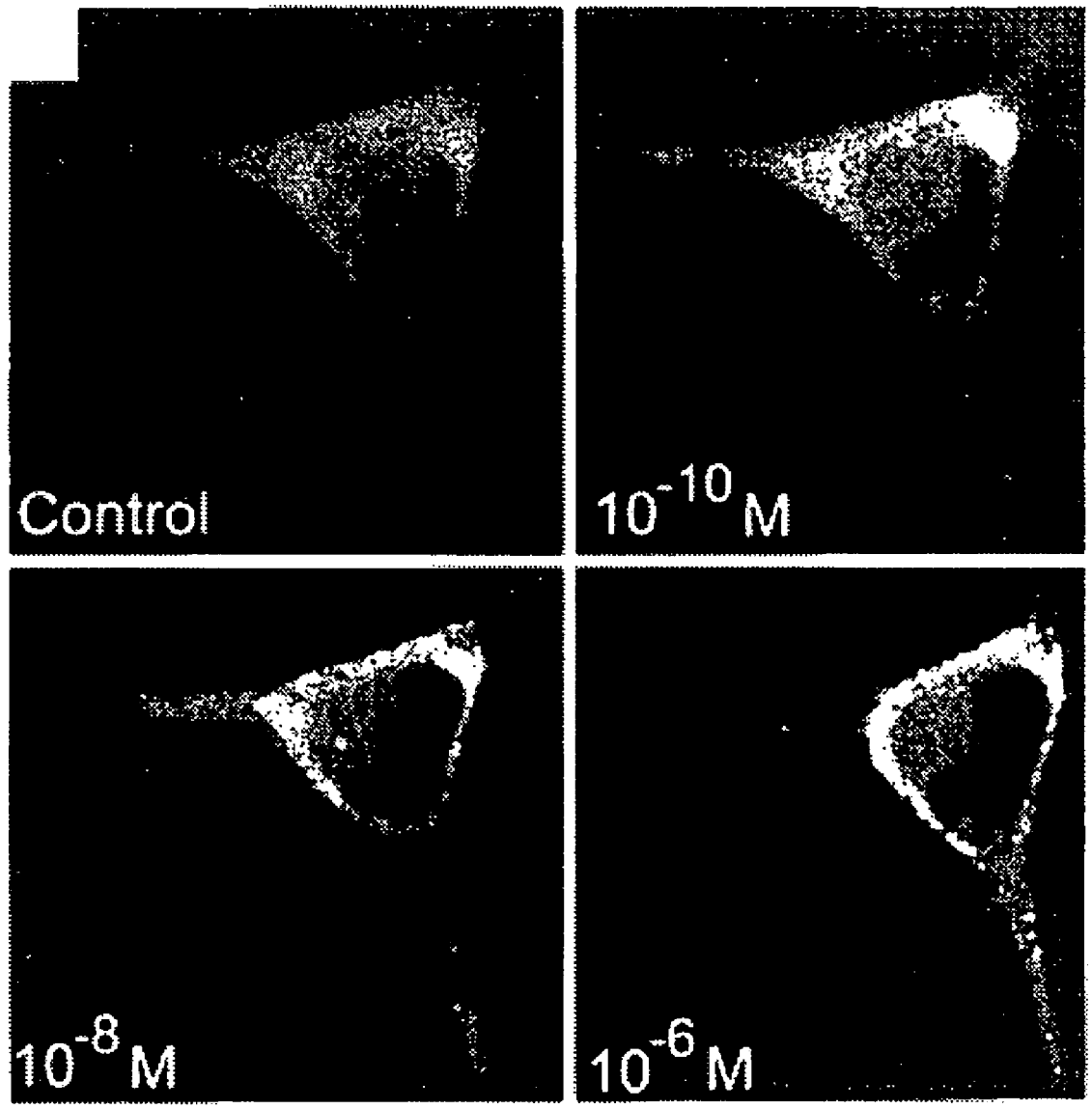
FIG. 6C is depicts the agonist-induced translocation of βarr2-GFP to beta2 adrenergic receptors in representational HEK-293 cells, at varying doses of agonist.
Figure 6E:
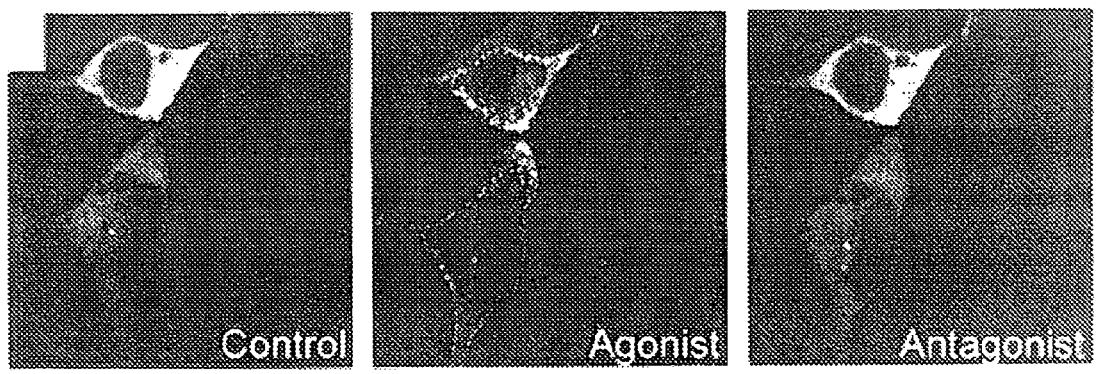
FIG. 6E evaluates the translocation of βarr2-GFP from the cell cytosol to the cell membrane, in response to exposure to receptor agonist (middle panel) and subsequent exposure to receptor antagonist (right panel).

The above experiments with COS and HEK-239 cells were reproduced except that the βAR2 antagonist propranolol was added to the cell medium. Using confocal microscopy to visually track βarr2-GFP in the cell in real time, as above, indicated that no shift in βarr2-GFP from cytosol to membrane occurred in response to a βAR2 antagonist. As shown in FIG. 6E, addition of an agonist (middle panel) resulted in translocation of βarr2-GFP from cytosol to membrane; subsequent addition of an antagonist (right panel) reversed the translocation (compare to control, left panel).

Biochemical evidence indicates that βarrestins are predominantly cytosolic proteins. Ferguson et al, *Can. J. Physiol. Pharmacol.* 74:1095 (1996). The present results confirm that βarr2-GFP is distributed throughout the cytosol and excluded from the nucleus. These data also establish that βarr2-GFP is not predominantly compartmentalized at the plasma membrane in the absence of agonist, but that upon exposure to an agonist the cellular βarr2-GFP shifts to the membrane. The present results further indicate that the shift of the βarr2-GFP conjugate in response to the addition of a G protein coupled receptor agonist can be detected optically as an enhancement of membrane fluorescence and/or a concomitant loss of cytosolic fluorescence, and that this response is rapidly observed.

EXAMPLE 6

Intracellular βarr2-GFP Targets Membrane Receptors

Figure 4A:
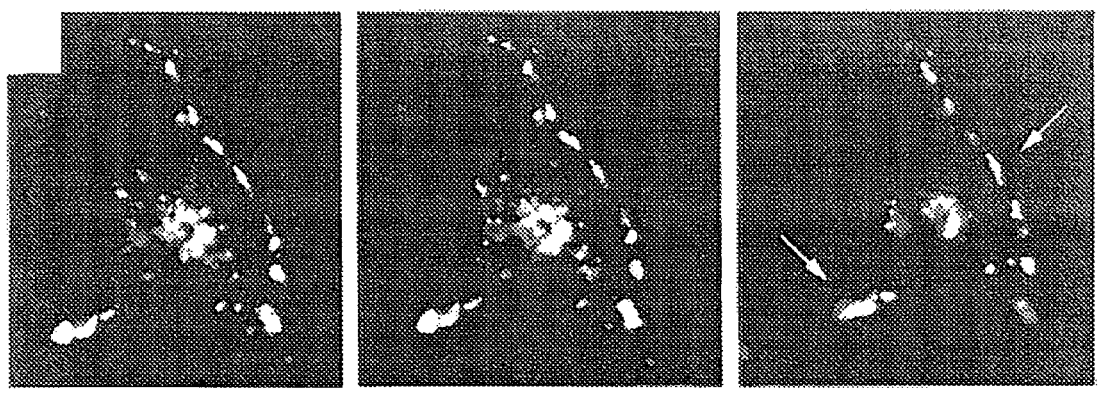
FIG. 4A shows a cell after reorganization of β2AR into plasma membrane clusters.
Figure 4B:
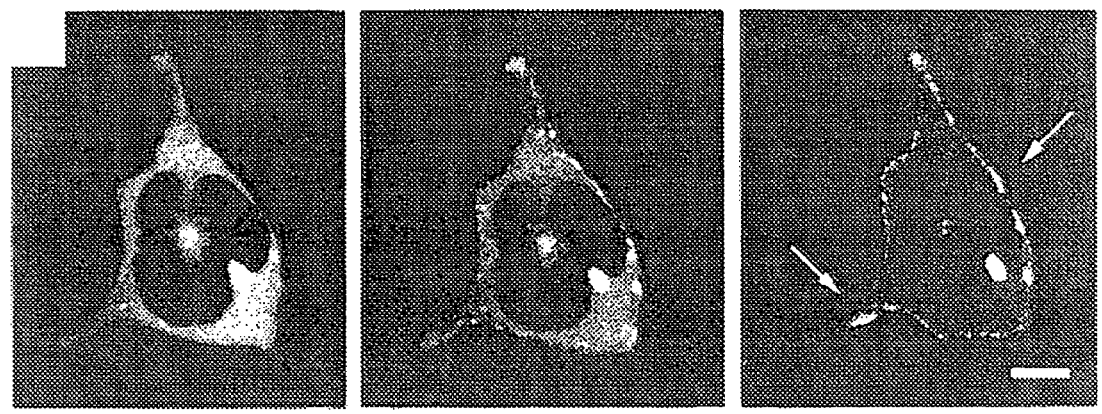
FIG. 4B provides three pictures of the same cell at 0, 3, and 10 minutes (left to right) after the addition of agonist. Redistribution of βarr2-GFP to the cell membrane is shown by the enhancement of membrane fluorescence with a concomitant loss of cytosolic fluorescence. Arrows indicate areas of co-localization; bar=10 microns.

FIG. 4 shows the time course of βarr2-GFP redistribution to plasma membrane 12CA5(HA) tagged β2AR in HEK-293 cells, as shown by confocal microscopy. The present example demonstrates that β2ARs are the target of intracellular βarr2-GFP conjugate proteins. HEK-293 cells containing 12CA5 (HA) tagged β2AR receptors were studied. The receptors in the HEK-293 cells were reorganized into plasma membrane clusters (Row A) by crosslinking with a mouse monoclonal antibody directed against an N-terminal epitope, followed by Texas Red conjugated goat anti-mouse antibody. In FIG. 4, the three panels of Row A show the same HEK-293 cell with βAR2 receptors reorganized into plasma membrane clusters.

HEK-293 cells were then exposed to agonist (isoproterenol added to cell medium, as above); the three panels of Row B in FIG. 4 were taken consecutively after agonist addition (left to right, at 0, 3 and 10 minutes post agonist addition). The real-time redistribution of βarr2-GFP to the receptors over a ten minute time period is thus demonstrated by comparing the panels of Row A and Row B of FIG. 4. In FIG. 4, arrows indicate areas of colocalization and the bar=10 microns.

FIG. 4 demonstrates that the geometry of the agonist-induced time dependent translocation of βarr2-GFP to the plasma membrane mimicked the distribution of pre-aggregated β2ARs. This indicates that the primary site targeted by βarrestin is the β2AR or a closely associated component.

EXAMPLE 7

Intracellular βarr2-GFP Targets Membrane Receptors

It has been postulated that phosphorylation of GPCRs by GRKs facilitates desensitization by increasing their affinity for βarrestins. Gurevich et al., *J. Biol. Chem.* 268:16879 (1993); Gurevich et al, *J. Biol. Chem.* 268:11628-11638 (1993); Ferguson et al., *Can. J. Physiol. Pharmacol.* 74:1095 (1996). When expressed in HEK-293 cells and exposed to agonist, mutant Y326A-β2ARs are not significantly phosphorylated by endogenous GRKs. Barak et al., *Biochem.* 34:15407 (1995); Ferguson et al., *J. Biol. Chem.* 270:24782 (1995). This phosphorylation impairment in Y326A-βAR2s is reversed by overexpression of GRKs in the same cell. Menard et al., *Biochem.* 35:4155 (1996). The Y326A mutant receptor was used to investigate βarrestin affinity in vivo; the effect of overexpressed GRK on the Y326A-B2AR interaction with βarr2-GFP was shown.

Y326A-β2AR and βarr2-GFP were co-transfected into HEK-293 cells, in the absence and presence of co-transfected GRK. If phosphorylation of GPCRs by GRKs facilitates desensitization by increasing their affinity for βarrestins, then overexpression of GRK would result in a noticeable difference in βarr2-GFP translocation.

Figure 5A:
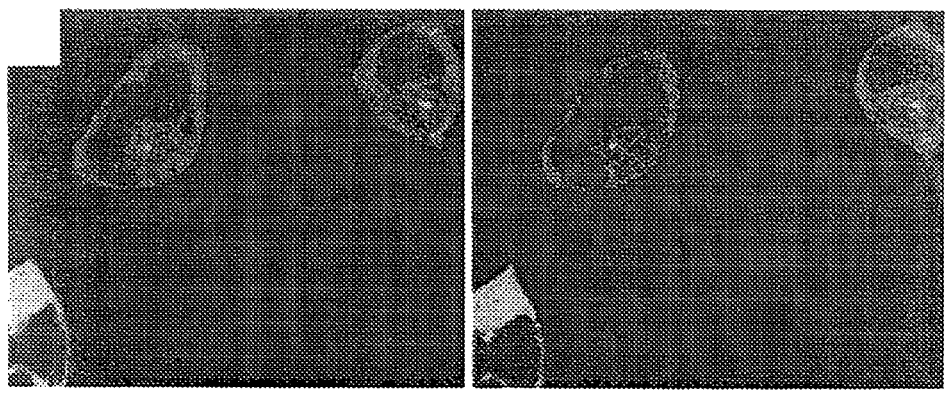
FIG. 5 shows the influence of overexpressed GRK on the redistribution of βarr2-GFP in HEK-293 cells expressing the Y326A phosphorylation-impaired β2AR. Cells without (Row A) and with (Row B) overexpressed GRKs were exposed to agonist, and the real-time redistribution of βarr2-GFP was observed. βarr2-GFP translocation in cells containing overexpressed GRK (Row B) was more robust, indicating an increased affinity of βarr2-GFP for receptor. Bar=10 microns.
Figure 5B:
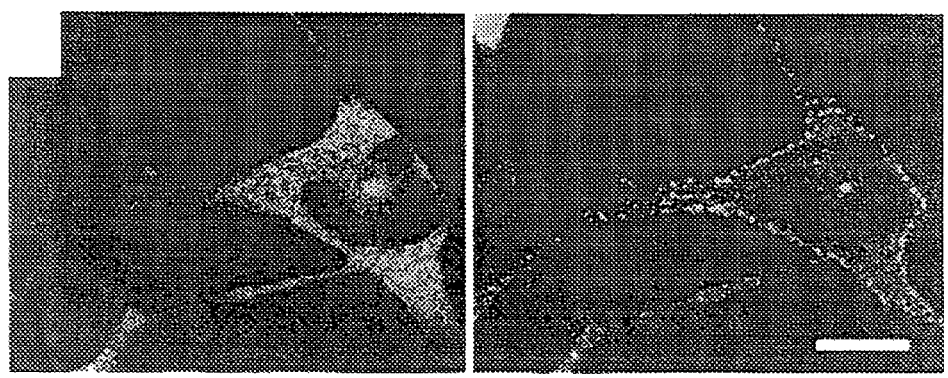

FIG. 5 shows the influence of overexpressed GRK on the redistribution of βarr2-GFP in HEK-293 cells expressing the Y326A phosphorylation impaired β2AR. Cells without (Row A) and with (Row B) overexpressed GRKs were exposed to agonist, and the real-time redistribution of βarr2-GFP was observed. Without added GRK, βarr2-GFP translocation in response to agonist proceeded poorly, as shown in Row A of FIG. 5. βarr2-GFP translocation in cells containing overexpressed GRK (Row B) was more robust, indicating an increased affinity of βarr2-GFP for receptor and the relationship of phosphorylation and βarrestin activity.

EXAMPLE 8

Testing of Additional Receptors in the βAR/rhodopsin Subfamily

Twelve different members of the βAR/rhodopsin subfamily of GPCRs have been studied. Cells expressing a particular GPCR, and containing βarrestin-GFP chimeric proteins were exposed to known agonists for the GPCR being studied. In each case, an observable translocation of the βarrestin-GFP chimeric proteins from the cell cytosol to the cell membrane was produced within minutes following addition of the GPCR agonist (data not shown).

EXAMPLE 9

Production of βArrestin Knockout Mice

Because GPCRs, such as the substance P receptor and the opioid receptors, participate in processing the sensation of pain, we characterized analgesic responses through the μ opioid receptor (μOR) in mice lacking βarrestin-2. In the clinical setting, morphine is currently the most effective drug for alleviating intense and chronic pain. The antinociceptive (blocking of pain perception) actions of morphine are mediated through stimulation of the μOR, as demonstrated by the lack of morphine analgesia observed in knock out mice deficient in the μOR(H. Matthes et al., *Nature* 383, 819 (1996). B. Kieffer, *Trends Pharmacol Sci* 20, 19 (1999); 1. Sora et al., *Proc Nad Acad Sci USA* 94, 1544 (1997)). Nevertheless, the neuronal signaling mechanisms mediating analgesia through μORs and morphine remain poorly understood. Moreover, the contribution of GPCR desensitization to the onset and duration of analgesia has been unclear.

βarrestin-2 knockout (βarr2-KO) mice were generated by inactivation of the gene by homologous recombination. A bacteriophage A library of mouse 129SvJ genomic DNA (Stratagene, La Jolla, Calif.) was screened with the rat βarr2 cDNA (H. Attramadal et al., *J. Biol. Chem.* 267,17882 (1992)). Positive phages were identified and analyzed by restriction digest. A 12-kb βarr2 fragment was digested with Bam HI, subcloned into pBluescript KS(−) and sequenced. The targeting vector was assembled by blunt-end ligation of a pHSV-TK cassette (from pIC19R/MCI-TK, M. R. Capecchi, University of Utah), a 2.8-kb Nco I-Bam HI βarr2 fragment, a pGK-neo cassette (from plasmid pD383, R. Hen, Columbia University) which replaced the 0.8 kb Bam HI-Hind III fragment of βarr2, and a 4.5 kb Hind III βarr2 fragment into pBluescript KS(−). This targeting vector was linearized with Not I and was electroporated into mouse embryonic stem cells. Genomic DNA from transfectants resistant to G418 and gancyclovir were isolated and screened by Southern (DNA) blot analysis using a 0.2 kb 5' external βarr2 probe and a 0.3 kb 3' external βarr2 probe. Chimeric animals were generated by microinjecting these ES cells into C57BL/6 blastocysts. Five chimeric male pups were obtained and mated with C57BL/6 females. Germline transmission was confirmed by Southern blotting. Heterozygous, offspring were intercrossed to obtain homozygous mice. Wild-type and mutant mice used in this study were age-matched, 3 to 5 month old, male siblings. For protein immunoblot analysis, whole cell lysates were prepared by polytron homogenization in lysing buffer [10 mM Tris (pH 7.4), 5 mM EDTA, 1 protease inhibitor tablet/10 mL (Roche Molecular Biochemicals, Indianapolis, Ind., USA), 1% nonidet-40]. Polyacrylamide gels were loaded with 25 μg protein/lane and equivalent protein loading was confirmed by Ponceau S staining of the gels. After transfer to polyvinyldifluoride (PVDF) membranes, proteins were blotted with polyclonal antibodies to βarrestin-2 or βarrestin-1 [H. Attramadal et al., *J. Biol. Chem.* 267, 17882 (1992)]. Bands were visualized with secondary antibody conjugated to horseradish peroxidase and an enhanced chemiluminescence detection system (Amersham, Piscataway, N.J.). All experiments were conducted in accordance with the NIH guidelines for the care and use of animals.

EXAMPLE 10

Identification of βArrestin Knockout Mice

Mice lacking βarrestin-2 were identified by Southern DNA blot analysis (FIG. 7A) and the absence of βarrestin-2 was confirmed by protein immunoblotting of extracts from brainstem, periaqueductal gray (PAG) tissue, spleen, lung and skin (FIG. 7B). Wild-type, heterozygous, and homozygous mutant mice had similar amounts of βarrestin-1 in the brain regions examined (FIG. 7B), arguing against compensatory upregulation of βarrestin-1 in the absence of βarrestin-2. The βarr2-KO mice were viable and had no gross phenotypic abnormalities. However, after administration of morphine, obvious differences became apparent between the genotypes.

EXAMPLE 11

Evaluation of Morphine-Induced Antinociception in βarrestin Knockout Mice

Figure 8:
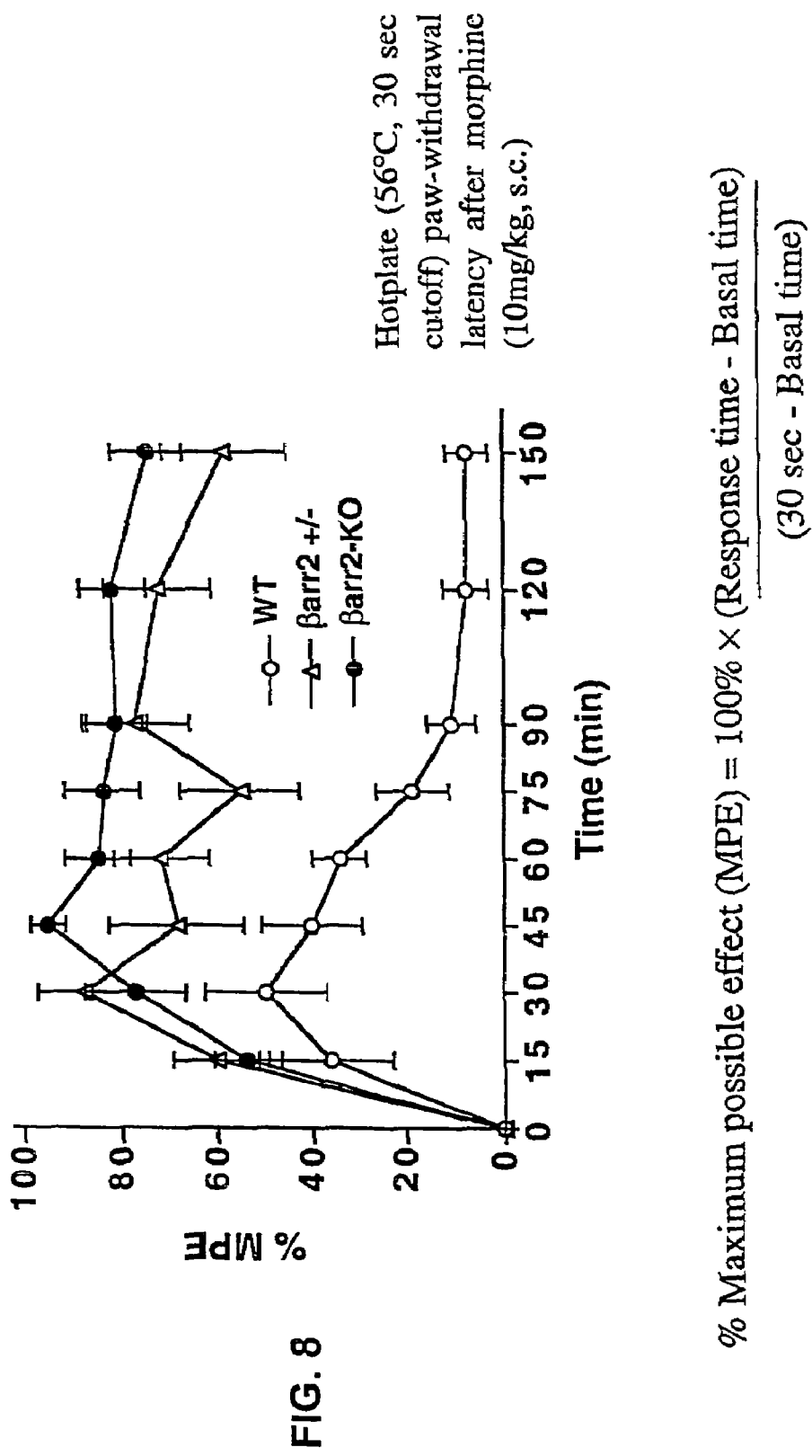
FIG. 8 illustrates enhanced and prolonged morphine-induced antinociception in βarr2-KO mice. Antinociceptive responses were measured as hot plate (56° C.) response latency after morphine (10 mg/kg, s.c.) treatment. The "response" was defined by the animal either licking the fore- or hind-paws or flicking the hind-paws. In these studies, the most prominent response was fore-paw licking. To avoid tissue damage the animals were not exposed to the plate for more than 30 seconds. Data are reported as the percent of the maximal possible response time (30 seconds) which was determined from each individual mouse's basal response, the response after drug treatment, and the imposed maximum cutoff time with the following calculation (F. Porreca et al., *J Pharmacol Exp Ther* 230, 341 (1984); J. Belknap et al., *Physiol Behav* 46, 69 (1989). M. Gardmark et al., *Pharmacol Toxicol* 83, 252 (1998); G. Elmer et al., Pain 75, 129 (1998)): 100% ×[(Drug response time-Basal response time)/(30 sec-Basal response time)]=% maximum possible effect (% MPE). WT (n=6), heterozygotes (+/−, n=5) and KO (n=9) mice were analyzed together in the same experiment. The % MPE curves of the βarr2-KO and βarr2+/−mice were significantly greater than the WT response curve (P<0.001) as determined by two-way ANOVA.

Morphine-induced antinociception was evaluated by measuring response latencies in the hot plate test. We used a dose of morphine (10 mg/kg) and route of administration (s.c.) well established to induce analgesia in many strains of mice (F. Porreca et al., *J Pharmacol Exp Ther* 230, 341 (1984). J. Belknap et al., *Physiol Behav* 46, 69 (1989). A Gardmark et al., *Pharmacol Toxicol* 83, 252 (1998). G. Elmer et al., *Pain* 75, 129 (1998)). The analgesic effect of morphine was significantly potentiated and prolonged in the knockout mice as compared to that in their wild-type littermates (FIG. 8). Such robust responses to morphine were not only absent in the wild-type liftermates (FIG. 8) but also in the parental mouse strains (C57BL/6 and 129SvJ) used to generate this knockout. Four hours after the morphine injection, βarr2-KO mice still exhibited significant analgesia (% maximum possible effect=31±0.4%); whereas, in control wild-type littermates, the analgesic effects of the same dose of morphine waned after about 90 minutes. βarr2+/−mice were nearly as responsive to morphine as the βarr2-KO mice; however, this may reflect the imposed limit of the hot plate assay (30 seconds), which is designed to prevent prolonged exposure of the mice to pain. Basal responses to the hot plate did not differ between genotypes (wild type: 6.2±0.3 sec., n=25; βarr2-KO: 6.1±0.4 sec., n=27). The differences in morphine-induced analgesia between the genotypes are unlikely to be due to pharmacokinetic differences in morphine metabolism, because the concentrations of morphine in blood, as determined by mass spectroscopy analysis, did not differ between wild type and βarr2-KO mice 2 hours after morphine injection (Mice were injected with morphine (10 mg/kg, subcutaneous). After 30 minutes or 2 hours, wild-type mice were killed and blood was collected in vials containing sodium fluoride and potassium-oxalate. Morphine concentration in blood samples pooled from 3 mice per sample were 1,500 ng/mL after 30 min., and 83 ng/mL blood after 2 hours as measured by mass spectroscopy analysis [Occupational Testing Division of LabCorp, Inc., Research Triangle Park, North Carolina, USA]. In similar experiments, βarr2-KO mice had a concentration of 93 ng/mL in the blood after 2 hours.

EXAMPLE 12

Evaluation of Low Dosage Morphine in βarrestin Knockout Mice

Figure 9:
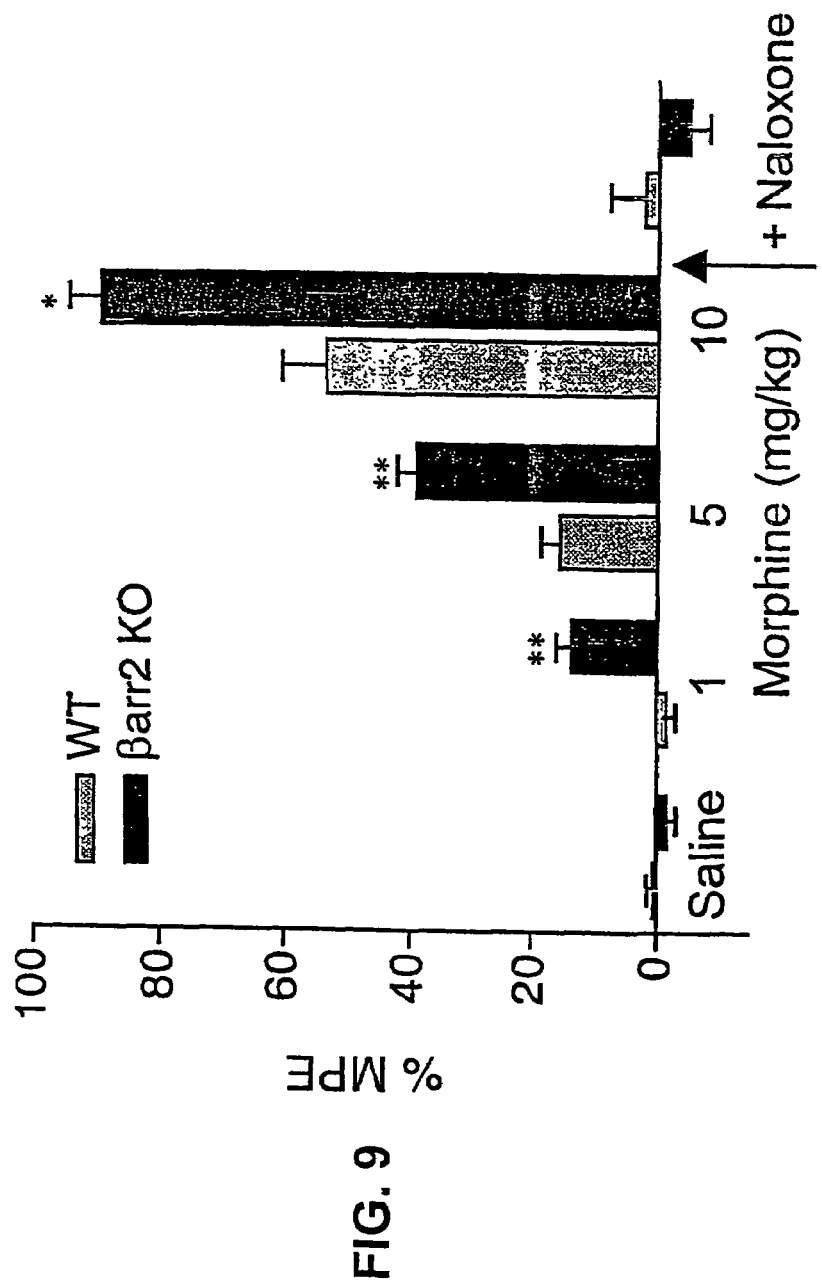
FIG. 9 depicts greater dose-dependent antinociceptive responses to morphine in βarr2-KO mice. The degree of antinociception was determined by measuring latency of hot plate (56° C.) responses (FIG. 2). Withdrawal latencies were measured 30 min. after a first dose of morphine (1 mg/kg, s.c.) at which point, animals were immediately injected with 4 mg/kg, s.c. morphine for a cumulative dose of 5 mg/kg. Antinociception was again assessed after 30 min. and mice were immediately injected with morphine (5 mg/kg, s.c.), to give a final cumulative dose of 10 mg/kg. Withdrawal latencies were again measured after 30 min. after which, mice were immediately injected with naloxone (2.5 mg/kg, s.c.). After 10 min., antinociception was assessed once more. WT (n=7) and βarr2-KO (n=6) mice were significantly different at each dose (*P<0.01, **P<0.001; Student's t-test). Means±S.E.M. are shown. In an additional experiment, morphine (25 mg/kg, s.c.) induced the maximum imposed response (100%) in both genotypes. Thus, an approximate 2 fold shift in the apparent $ED_{50}$ values was observed between genotypes [WT: 9.77 (8.08-11.81) mg/kg; KO: 5.98 (5.10-6.94) mg/kg (95% confidence intervals)].

Lower doses of morphine were also tested in these assays. Even at doses of morphine (1 mg/kg, s.c.) that were sub-analgesic in wild type mice, βarr2-KO animals displayed a significant increase in their nociceptive thresholds (FIG. 9). At 30 minute intervals, immediately following the antinociception test, mice were given repeated cumulative doses of morphine resulting in final concentrations of 5, and 10 mg/kg (I. Sora et al., *Proc Natl Acad Sci USA* 94, 1544 (1997)). At the highest cumulative dose, mice reached similar levels of antinociception as seen in FIG. 8, in which this amount of morphine was administered in a single injection. At every dose, the βarr2 KO animals experienced greater antinociception after morphine treatment than did their wild-type littermates.

EXAMPLE 13

Evaluation of Morphine Antagonists in βarrestin Knockout Mice

To test whether the analgesic effects of morphine were mediated by actions at the μOR, mice were treated with various antagonists. Naloxone (2.5 mg/kg, subcutaneous injection) which immediately reverses the effects of opiates, was given 30 minutes after morphine (10 mg/kg). Naltrindole [P. Portoghese et al., *J Med Chem.* 88, 1547 (1990)] was given 20 minutes before morphine, and norbinaltorphimine (A. Takemori et al., *J Pharmacol Exp Ther* 246, 255 (1988)) was given 1 hour before morphine (H. Matthes et al., *J Neurosci* 18, 7285 (1998)). Naloxone, a well-established OR antagonist, was administered to the same mice, immediately after measuring the antinociceptive effects of morphine (10 mg/kg). Naloxone (2.5 mg/kg, s.c.) completely reversed the effects of morphine in both the wild-type and βarr2-KO animals within 10 minutes. However, the σ and κ OR-selective antagonists naltrindole (2.5 mg/kg, s.c.) and nor-binaltorphimine (5 mg/kg s.c.) did not inhibit analgesia in wild type nor βarr2-KO mice (data not shown). The morphine dose dependency of the antinociceptive response and the reversal of the effects with naloxone suggest that the potentiated and prolonged effects in mice that lack βarrestin-2 result from stimulation of the μOR.

EXAMPLE 14

Body Temperature Measurements in Wild-Type and βarrestin Knockout Mice

Figure 10:
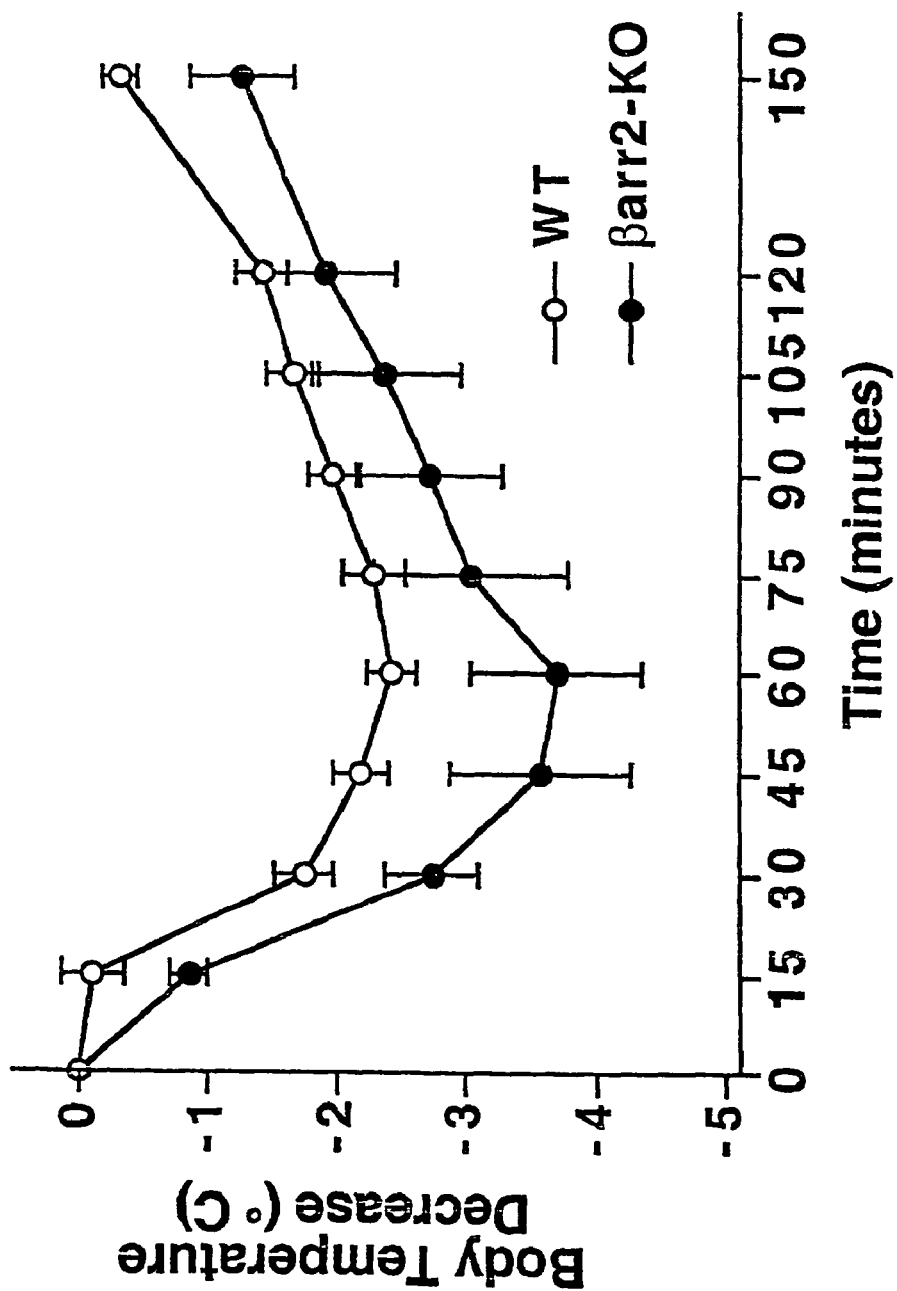
FIG. 10 depicts increased hypothermic responses to morphine in βarr2-KO mice. Rectal body temperatures were measured with a digital thermometer (M. Adler et al., *Annu Rev Pharmacol Toxicol* 28, 429 (1988); F. Fumagalli et al., *J Neurosci* 18, 4861 (1998) (TH8, Physitemp, Clifton, N.J., USA). The probe was inserted into the rectum and maintained until the temperature reading stabilized. Basal body temperatures did not vary significantly between genotypes (WT: 36.4±0.1° C.; KO: 36.8±0.1° C.). VVT (n=5) and KO (n=5) animals were analyzed in parallel during the same experiment. The curves are significantly different (P<0.001) as determined by 2-way ANOVA. Means±S.E.M. are shown.

Wild-type and βarr2-KO mice were also evaluated for changes in body temperature (M. Adler et al., *Annu Rev Pharmacol Toxicol* 28, 429 (1988). Rectal body temperatures were determined with a digital thermometer [F. Fumagalli et al., *J Neurosci* 18, 4861 (1998)] (TH8, Physitemp, Clifton, N.J., USA). The probe was inserted into the rectum and maintained until the temperature reading stabilized. No significant differences in basal body temperature were found between genotypes, however βarr2-KO mice experienced a greater drop in body temperature after morphine treatment than did wild-type (FIG. 10). This greater decrease in temperature also persisted longer than that in their wild type littermate controls.

EXAMPLE 15

Radioligand Binding Assays

To investigate whether the μOR population was altered in the KO mice, radioligand binding analysis on membranes prepared from different brain regions was performed. Brain regions were dissected and immediately frozen in liquid nitrogen and were stored at −80° C. for less than 1 week before use. Samples were placed on ice and homogenized by polytron in membrane preparation buffer [50 mM Tris (pH 7.4), 1 mM EDTA, 3 mM MgCl$_2$] and crude membranes were prepared by centrifugation at 20,000×g for 15 min at 4° C. Membranes were resuspended in either 50 mM Tris-HCl (pH 7.4) for radioligand binding assays or in assay buffer [50 mM Tris-HCl (pH 7.4), 100 mM NaCl, 3 mM MgCl$_2$, 0.2 mM EDTA] containing 10 μM GDP for [$^{35}$S] GTPγS binding assays. For both binding assays, reactions were terminated by rapid filtration over GF/B filters (Brandel, Inc., Gaithersburg, Md.) using a Brandel cell harvester (Brandel, Inc., Gaithersburg, Md.). Filters were washed 3 times with ice cold 10 mM Tris-HCl (pH 7.4) and then counted in a liquid scintillation counter. Hypothalamus, brain stem, and periaqueductal gray (PAG) regions were chosen because they contain μORs and are implicated in the regulation of pain and body temperature (D. Mayer and D. Price, *Pain* 2, 379 (1976). T. Yaksh et al., *Prog Brain Res* 77, 371 (1988). D. J. Smith., et al., *Eur J Pharmacol* 156, 47 (1988)). Data are given in Table I. Saturation binding studies with $^3$H-naloxone, at concentrations that preferentially label the μOR, revealed a single high affinity binding site, which represents the μOR. The number and affinity of μORs did not significantly differ between the two genotypes in any of the brain regions examined.

TABLE I

H-Naloxone binding in brain regions of Wild Type and Knockout mice.[1]

| Brain region | Wild Type | | βarr2-Knockout | |
|---|---|---|---|---|
| | $B_{MAX}$ (fmol/mg) | $K_D$ (nM) | $B_{MAX}$ (fmol/mg) | $K_D$ (nM) |
| PAG | 132 ± 9 | 4.0 ± 0.1 | 144 ± 13 | 3.0 ± 0.8 |
| Brainstem | 49 ± 7 | 1.5 ± 0.2 | 54 ± 9 | 3.0 ± 0.8 |
| Hpothalamus | 103 ± 18 | 6.2 ± 1.6 | 89 ± 8 | 3.8 ± 0.2 |

[1] Saturation binding assays were performed on membranes from different brain regions (50-100 μδ/tube) with increasing concentrations of $^3$H-naloxone (0-12 nM, 52.5 Ci/mmol, Amersham, Piscataway, New Jersey, USA). Nonspecific binding was determined in the presence of 10 μM naloxone. Membranes were incubated at 25° C. for I hour. Binding parameters were determined via Scatchard analysis of specific binding. Data are the mean ± S.E.M. of 3-4 experiments performed in duplicate.

Figure 11:
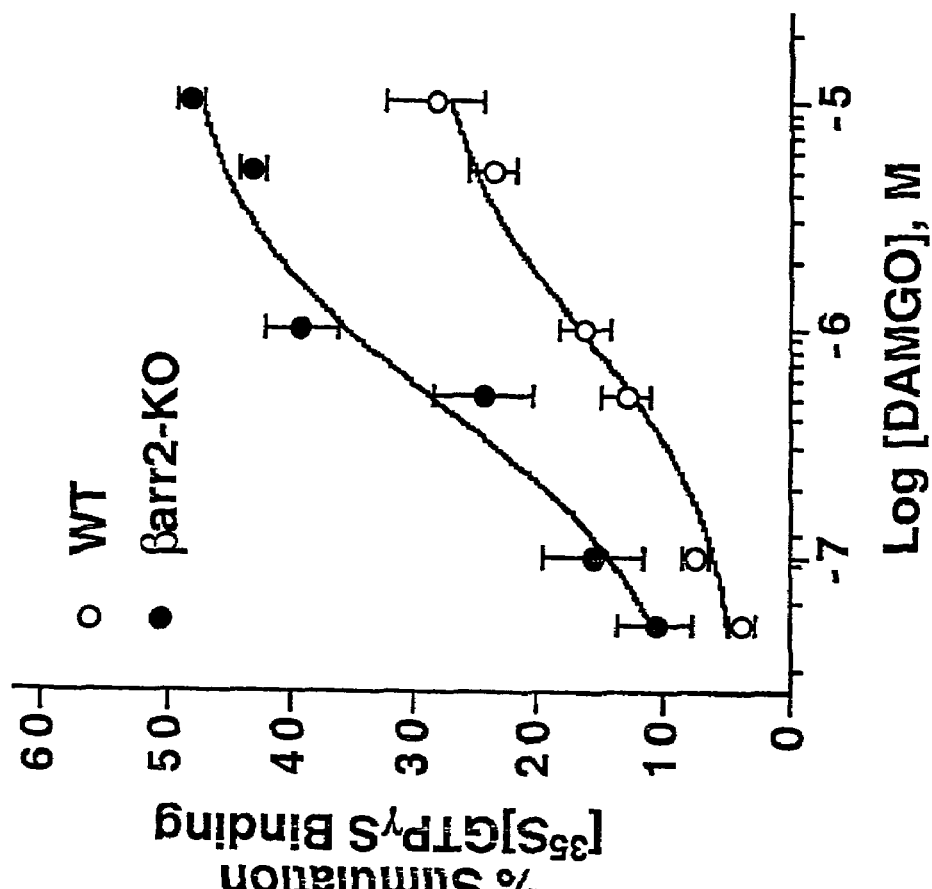
FIG. 11 illustrates binding of [$^{35}$S]GTPγS to periaqueductal gray membranes from βarr2-KO and wild type (WT) mice. [$^{35}$S]GTPγS binding to isolated periaqueductal gray (PAG) membranes (prepared as described in conjunction with Table 1 below) was determined after 2 hour stimulation (30° C.) with 50-10,000 nM of the mOR-selective agonist, [D-Ala2, MePhe4, Gly5-ol]enkephalin (DAMGO). PAG membranes (10 μg protein per assay tube) were incubated in the presence of 10 μM GDP and 50 pM [$^{35}$S]GTPγS (1250 Ci/mmol, NEN, Boston, Mass.). [$^{35}$S]GTPγS binding was measured as described (P. Portoghese, in *Handbook of Experimental Pharmacology: Opioids* 1, A. Herz, Ed. (Springer-Verlag, New York, 1993) p.p. 279293. A. et al., ibid, p.p. 645-679). [$^{35}$S]GTPγS binding is expressed as percent increase in [$^{35}$S] GTPγS binding relative to binding in unstimulated samples. Data were analyzed by nonlinear regression using GraphPad Prism software and are presented as the mean±S.E.M of at least three experiments performed in triplicate wherein WT and βarr2-KO brain regions were assayed simultaneously. In the absence of agonist stimulation, basal [$^{35}$S]GTPγS binding was: WT: 440±83 cpm and βarr2-KO: 527±99 cpm.
Figure 11:
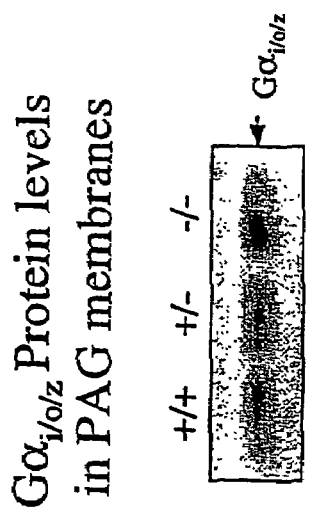

Additional evidence for increased sensitivity of the μOR in βarr2-KO animals was obtained in biochemical experiments. We measured agonist-stimulated binding of [$^{35}$S]GTPγS to G proteins in isolated membranes the most proximal manifestation of GPCR activation (D. Selley et al., *Mol Pharmacol* 51, 87 (1997)). Because morphine acts in vitro to stimulate μ, σ, and κ opioid receptors, the μOR-selective agonist, [D-Ala$^2$, MePhe$^4$, Gly$^5$-ol]enkephalin (DAMGO), was used to specifically activate G protein coupling to μORs. DAMGO stimulated more [$^{35}$S]GTPγS binding in membranes derived from βarr2-KO mice than in those derived from wild-type littermates (FIG. 11). Similar results were also obtained in brainstem membranes (data not shown). The amount of Gα proteins ($G_{i/o/z}$) as determined by protein immunoblotting, did not vary between the genotypes (data not shown). These observations suggest that there is enhanced coupling of μORs to G proteins in tissues derived from βarr2-KO mice. Although the enhanced analgesia induced by morphine may involve complex neurological-signaling, this biochemical evidence supports the interpretation that the enhanced physiological responsiveness in the knockout animals results from increased sensitivity of signaling by the μOR.

These studies demonstrate in an animal model that the absence of βarrestin-2 can affect the efficacy of GPCR activation. In transfected cultured cells, the degree of β$_2$-adrenergic receptor signaling is dependent upon the cellular complement of GRK2 and GRK3 and βarrestins (L. Menard et al., *Mol Pharmacol* 51, 800 (1997); S. Mundell et al., *Biochemistry* 38, 8723 (1999)). These observations, along with those presented here, directly support the proposed role of βarrestin-2 in preventing further receptor-G protein coupling and mediating desensitization of the GPCR. Moreover, βarrestins are not only involved in the dampening of GPCR responsiveness after agonist stimulation, but also influence the sensitivity of the response.

The simplest interpretation of these results is that μOR signaling is regulated by βarrestin-2. However, in transfected cells, morphine fails to induce the internalization of the μOR and a GFP-tagged βarrestin-2 fails to translocate to μOR overexpressed in cell culture upon exposure to morphine (J. Arden et al., *J Neurochem* 65, 1636 (1995). D. Keith et al., *J Biol Chem* 271, 19021 (1996); J. Whistler and M. von Zastrow, *Proc Natl Acad Sci USA* 95, 9914 (1998); J. Zhang et al., *Proc Natl Acad Sci USA* 95, 7157 (1998)). Interestingly, these in vitro studies have been conducted with the rat μOR or the mouse MOR1 which are not particularly rich in potential phosphorylation sites. Several splice variants of the μOR are present in mouse brain that contain several potential phosphorylation sites (Y. Pan et al., *Mol Pharmacol* 56, 396 (1999)). Some of these isoforms can contribute to morphineinduced analgesia. The involvement of these receptors might explain the differences between the in vitro studies and those with the βarr2-KO mice.

The βarr2-KO mice were very similar in phenotype to their wild type littermates and other GPCR-directed drugs did not necessarily elicit different responses between the genotypes. For example, locomotor responses to dopamine receptor stimulation by cocaine and apomorphine were not enhanced (data not shown). These observations suggest that various GPCRs are differentially affected by the loss of βarrestin-2. Other regulatory elements, such as GRKs or βarrestin-1, could compensate for the lack of βarrestin-2, or the receptors could vary in their requirement for βarrestin interaction for their regulation.

The foregoing is illustrative of the present invention, and is not to be construed as limiting thereof. The invention is defined by the following claims, with equivalents of the claims to be included therein.

That which is claimed:

1. A conjugate comprising a β-arrestin protein and a label, wherein said label is capable of indicating intracellular translocation and/or distribution of said β-arrestin protein, wherein said β-arrestin is capable of interacting with a G protein coupled receptor (GPCR).

2. The conjugate according to claim 1, wherein said conjugate is a fusion protein.

3. The conjugate of claim 1, wherein said label is an optically detectable label.

4. A conjugate comprising a β-arrestin-2 protein and a label, wherein said label is capable of indicating intracellular translocation and/or distribution of said β-arrestin-2 protein, wherein said β-arrestin-2 is capable of interacting with a G protein coupled receptor (GPCR).

5. The conjugate according to claim 1, wherein said label is a fluorescent label.

6. The conjugate according to claim 1, wherein said label is a colorimetric label.

7. The conjugate according to claim 1, wherein said label is a radioactive label.

8. The conjugate according to claim 1, wherein said label is an electron-dense label.

9. The conjugate according to claim 5, wherein said fluorescent label is Green Fluorescent Protein (GFP).

* * * * *